US012584926B2

(12) United States Patent
Srinivasan et al.

(10) Patent No.: US 12,584,926 B2
(45) Date of Patent: Mar. 24, 2026

(54) METHODS FOR IDENTIFYING HAEMOGLOBIN S OR C IN A BIOLOGICAL SAMPLE AND KITS THEREOF

(71) Applicant: Indian Institute of Science, Bangalore (IN)

(72) Inventors: Rajesh Srinivasan, Bangalore (IN); Eugene Christo V R, Bangalore (IN); Prateek Katare, Bangalore (IN); Aravind Venukumar, Bangalore (IN); Sai Siva Gorthi, Bangalore (IN); Nisanth KM Nambison, Bhopal (IN)

(73) Assignee: Indian Institute of Science, Bangalore (IN)

( * ) Notice: Subject to any disclaimer, the term of this patent is extended or adjusted under 35 U.S.C. 154(b) by 1053 days.

(21) Appl. No.: 17/684,777

(22) Filed: Mar. 2, 2022

(65) Prior Publication Data

US 2022/0283188 A1     Sep. 8, 2022

(30) Foreign Application Priority Data

Mar. 3, 2021     (IN) ............................. 202141009024

(51) Int. Cl.
*G01N 33/72*     (2006.01)
*G01N 21/31*     (2006.01)
*G01N 33/49*     (2006.01)

(52) U.S. Cl.
CPC ........... *G01N 33/721* (2013.01); *G01N 21/31* (2013.01); *G01N 33/49* (2013.01); *G01N 2333/805* (2013.01); *G01N 2800/22* (2013.01)

(58) Field of Classification Search
CPC .. G01N 33/49; G01N 33/721; G01N 33/6893; G01N 21/31; G01N 21/314; G01N 2333/805; G01N 2800/22
USPC ................ 436/63, 66, 164; 422/82.05, 82.09
See application file for complete search history.

(56) References Cited

U.S. PATENT DOCUMENTS

| | | | |
|---|---|---|---|
| 8,623,659 B2 | 1/2014 | Randolph | |
| 9,995,757 B2 | 6/2018 | Rice et al. | |
| 10,690,652 B2 | 6/2020 | Znaty et al. | |
| 2005/0118654 A1* | 6/2005 | Blomberg .............. | C07K 16/18 |
| | | | 530/391.1 |
| 2015/0323521 A1* | 11/2015 | Randolph ............ | G01N 33/721 |
| | | | 435/29 |
| 2024/0241141 A1* | 7/2024 | Gurkan .................. | G01N 21/31 |

FOREIGN PATENT DOCUMENTS

| | | |
|---|---|---|
| EP | 3076333 A1 | 10/2016 |
| WO | WO2019202410 A1 | 10/2019 |

OTHER PUBLICATIONS

Akuwudike et al., Absorption Spectra of Normal Adult and Sickle Cell Haemoglobins Treated With Hydrogen Peroxide at Two pH Values, Adv. Biores. vol. 1 [2] Dec. 2010, p. 55-60.
Almulla et al., Visible and near-infrared absorption properties of blood from sickle cell patients and normal Individuals, Royal College of Surgeons in Ireland Student Medical Journal 2011;4(1):82-83.
Bond et al., Towards a point-of-care strip test to diagnose sickle cell anemia, PLoS One. May 16, 2017;12(5): e0177732.
Hockham et al., The spatial epidemiology of sickle-cell anaemia in India, Sci Rep 8, 17685 (2018).
Masilamani et al., Spectral detection of sickle cell anemiaand thalassemia, Photodiagnosis Photodyn Ther. Dec. 2013;10(4):429-33.
Masilamani et al., A Novel Technique of Spectral Discrimination of Variants of Sickle Cell Anemia, Disease Markers, vol. 2018, Article ID 5942368, 7 pages, 2018.
Patel et al., Oxygen Dissociation Assay (ODA): spectrophotometric based screening platform for hemoglobin-O2 affinity modifiers, BMG Labtech Resources Application notes AN337, Rev. Jun. 2019.
Piety et al., A Paper-Based Test for Screening Newborns for Sickle Cell Disease, Sci Rep. Apr. 3, 2017;7:45488.
Randolph et al., Novel Test Method (Sickle Confirm) to Differentiate Sickle Cell Anemia from Sickle Cell Trait for Potential Use in Developing Countries, Clin Lab Sci. Winter 2012;25(1):26-34.
Yang et al., A simple, rapid, low-cost diagnostic test for sickle cell disease, Lab Chip. Apr. 21, 2013;13(8):1464-7.

* cited by examiner

*Primary Examiner* — Maureen Wallenhorst
(74) *Attorney, Agent, or Firm* — Bret E. Field; Bozicevic, Field & Francis LLP

(57) ABSTRACT

The present disclosure provides in vitro methods for identifying the presence or absence of haemoglobin S (HbS) or haemoglobin C (HbC) in a blood sample, kits and devices thereof. The inventors have found that HbS shows a substantial decrease in absorption under deoxygenated conditions compared to oxygenated conditions. The inventors expect HbC to show a similar decrease in absorption under deoxygenated conditions compared to oxygenated conditions. The methods, kits and devices of the disclosure employ this decrease in absorption under deoxygenated conditions to identify the presence or absence of HbS or HbC in a blood sample. The methods, kits and devices of the present disclosure are simple, low cost, and provide a rapid way to identify the presence or absence of HbS or HbC in a blood sample in a point-of-care setting.

9 Claims, 3 Drawing Sheets

METHODS FOR IDENTIFYING HAEMOGLOBIN S OR C IN A BIOLOGICAL SAMPLE AND KITS THEREOF

TECHNICAL FIELD

The present disclosure relates to the field of identifying the presence or absence of haemoglobin S (HbS) and/or or haemoglobin C (HbC) in a blood sample. More particularly, the disclosure relates to a method comprising measuring absorbance of the blood sample under different conditions, calculating a ratio of absorbance or a percent reduction in absorbance under said conditions, and identifying the presence or absence HbS and/or HbC based on said ratio or percent reduction.

BACKGROUND OF THE DISCLOSURE

Sickle cell disease (SCD) is a genetic disorder associated with the haemoglobin protein of Red Blood Cells (RBCs). SCD is inherited in an autosomal recessive pattern and is considered among the most commonly inherited diseases worldwide. The cause of SCD is a point mutation in the beta-globulin gene (of haemoglobin), which results in the substitution of glutamic acid with valine (sixth position of beta-globin chain). Haemoglobin with this defect is referred to as HbS as opposed to the normal adult haemoglobin, HbA. Some individuals carry another point mutation in a haemoglobin gene resulting in production of haemoglobin C (HbC) which also causes sickling of RBCs. The amino acid substitution alters the conformation of the haemoglobin S (HbS) or haemoglobin C (HbC) under hypoxic conditions, exposing a hydrophobic patch on the haemoglobin surface. This leads to polymerization of defective haemoglobin proteins within the RBC to form elongated rope-like fibers that distort the normal biconcave disc shape RBCs to sickle or crescent shape under hypoxic conditions. These abnormal sickle-shaped RBCs are rigid and sticky, so they may get trapped in small blood vessels (capillaries) that trigger acute painful events, depriving tissues of oxygen-rich blood and damaging organs, most notably, the spleen. The trapped RBCs eventually rupture, resulting in the reduced lifespan of the RBCs in SCD patients (10-20 days), as opposed to healthy individuals (120 days). Hence, SCD patients are characterized by anemia, having decreased haemoglobin concentration and RBC count.

SCD is considered to be a disorder of global importance with economic as well as clinical significance. People affected by this disease are scattered across Sub-Saharan Africa, the Middle East, India, Caribbean, South and Central America, some countries along the Mediterranean Sea, as well as in the United States and Europe. In the United States, 80,000-100,000 individuals are affected by the disorder. Worldwide, more than 300,000 children are estimated to be born annually with sickle cell disease. In India, it is prevalent in Chhattisgarh, Odisha, Maharashtra, Gujarat, Madhya Pradesh, Telangana, Andhra Pradesh and some parts of Tamil Nadu and Kerala.

Sickle cell disorder can be classified into two categories namely, sickle cell trait (SCT) and sickle cell disease (SCD) based on the zygosity. Since sickle cell disorder is an autosomal recessive disorder, the offspring has to inherit defective genes from both father and mother to be affected by the disease. If the abnormal beta-globin gene is inherited from both parents, the condition is referred to as SCD (homozygous) and if only one abnormal beta-globin gene is inherited (heterozygous), then the condition is referred to as SCT. People with SCT are usually asymptomatic but are carriers of the abnormal gene and have a 50% probability to pass it to their progeny.

Sickle cell diagnostic tests are grouped into two categories namely, screening tests and confirmatory tests. The solubility test is a widely used screening test. It is a simple and cost-effective test that helps to screen a large population to differentiate healthy individuals from individuals with sickle cell disorder. Solubility test involves the addition of blood with freshly prepared reagents and visual inspection for turbidity of the solution. Samples from healthy individuals are transparent, whereas sickle-cell samples appear turbid. This simple test can be performed at point-of-need as it requires very less quality of blood and does not require any sophisticated equipment or power. However, they cannot be used to differentiate between SCT and SCD conditions. Hence, samples tested positive in the screening tests need to be processed further by confirmatory tests to predict the zygosity.

Confirmatory tests help to distinguish between sickle cell trait and sickle cell disease and also provide the concentration of Haemoglobin variants (HbS, A, F, etc.). Since there is no easily available cure for SCD, disease management and treatment are aimed to improve the anemic condition to reduce complications. Confirmatory test results help in deciding the treatment regime and also monitor the effectiveness of treatment. There are numerous tests available under confirmatory tests, e.g., High-pressure liquid chromatography (HPLC), Isoelectric focusing (IEF), Hb Electrophoresis, and molecular diagnostic test (RFLP). Though these tests are highly specific and provide both qualitative and quantitative results, they are expensive, time-consuming, and require specialized laboratories with trained personnel to operate the device. These confirmatory tests cannot be tested at point-of-care. Hence, there is a need for the development of a portable point-of-care system that can perform both screening and confirmatory tests (i.e., predict zygosity) for SCT/SCD which can be used in low-resource settings.

India is estimated to have the second largest burden of SCD with an estimate of 42,016 predicted sickle cell anemia births per year (estimated in 2010). Though sickle cell anemia has a widespread geographical distribution, it is highly prevalent among the tribal population. According to a census report in 2011, the tribal population in India is approximately 104 million. It is estimated that between 1 to 40% of the tribal population in India are affected by sickle cell anemia. Since these affected areas are remote, current testing methods (confirmatory test to identify SCT/SCD) involve transporting the blood samples to a centralized laboratory, which is burdensome and time-consuming Hence there is a strong need for point-of-care, portable, low cost, rapid testing methods, kits, and devices capable of performing identification of HbS and HbC and identification of SCT and SCD or other sickle cell conditions. The present disclosure attempts to address this need by providing methods, kits, and devices capable of operating in low resource settings for identifying the presence or absence of HbS and HbC and the presence of absence of SCT or SCD in a subject.

STATEMENT OF THE DISCLOSURE

In some embodiments, the present disclosure provides an in vitro method of identifying the presence or absence of haemoglobin S (HbS) or haemoglobin C (HbC) in a blood sample, comprising: (a) measuring a first absorbance of said blood sample under a deoxygenated condition at a wavelength selected from 420-440 nm; (b) measuring a second absorbance of said blood sample under the deoxygenated condition at a wavelength selected from 545-565 nm; (c) calculating a ratio of the second absorbance to the first absorbance or a ratio of the first absorbance to the second absorbance; and (d) identifying the presence or absence of HbS or HbC in said blood sample based on the ratio In some embodiments, the present disclosure provides an in vitro method of identifying the presence or absence of HbS or HbC in a blood sample, comprising: (a) mixing said blood sample with a physiologically acceptable buffer comprising a detergent and a reducing agent to obtain a sample-buffer mixture; (b) measuring a first absorbance of the sample-buffer mixture at a wavelength selected from 420-440 nm; (c) measuring a second absorbance of the sample buffer mixture at a wavelength selected from 545-565 nm; (d) calculating a ratio of the second absorbance to the first absorbance or a ratio of the first absorbance to the second absorbance; and (e) identifying the presence or absence of HbS or HbC in said blood sample based on the ratio.

In some embodiments, the present disclosure provides an in vitro method of identifying the presence or absence of HbS or HbC in a blood sample, said method comprising: (a) measuring a first absorbance of said blood sample under an oxygenated condition at a wavelength selected from 408-418 nm; (b) measuring a second absorbance of said blood sample under a deoxygenated condition at a wavelength selected from 422-432 nm; (c) calculating a percent reduction in the second absorbance compared to the first absorbance; and (d) identifying the presence or absence of HbS or HbC in said blood sample based on the percent reduction.

In some embodiments, the present disclosure provides an in vitro method of identifying the presence or absence of HbS or HbC in a blood sample, comprising: (a) mixing a first part of said blood sample with a first physiologically acceptable buffer comprising a detergent to obtain a first sample-buffer mixture; (b) measuring a first absorbance of the first sample-buffer mixture at a wavelength selected from 408-418 nm; (c) mixing a second part of said blood sample with a second physiologically acceptable buffer comprising a detergent and a reducing agent to obtain a second sample-buffer mixture; (d) measuring a second absorbance of the second sample-buffer mixture at a wavelength selected from 422-432 nm; (e) calculating a percent reduction in the second absorbance compared to the first absorbance; and (f) identifying the presence or absence of HbS or HbC in said blood sample based on the percent reduction.

In some embodiments, the present disclosure provides an in vitro method identifying the presence or absence of sickle cell trait (SCT) or sickle cell disease (SCD) in a subject, said method comprising: (a) measuring a first absorbance of a blood sample from the subject under a deoxygenated condition at a wavelength selected from 420-440 nm; (b) measuring a second absorbance of said blood sample under the deoxygenated condition at a wavelength selected from 545-565 nm; (c) calculating a ratio of the second absorbance to the first absorbance or a ratio of the first absorbance to the second absorbance; and (d) identifying the presence or absence of SCT or SCD in the subject based on the ratio.

In some embodiments, the present disclosure provides an in vitro method identifying the presence or absence of SCT or SCD in a subject, said method comprising: (a) mixing a blood sample from the subject with a physiologically acceptable buffer comprising a detergent and a reducing agent to obtain a sample-buffer mixture; (b) measuring a first absorbance of the sample-buffer mixture at a wavelength selected from 420-440 nm; (c) measuring a second absorbance of the sample buffer mixture at a wavelength selected from 545-565 nm; (d) calculating a ratio of the second absorbance to the first absorbance or a ratio of the first absorbance to the second absorbance; and (e) identifying the presence or absence of SCT or SCD in the subject based on the ratio.

In some embodiments, the present disclosure provides an in vitro method identifying the presence or absence of SCT or SCD in a subject, said method comprising: (a) measuring a first absorbance of a blood sample from the subject under an oxygenated condition at a wavelength selected from 408-418 nm; (b) measuring a second absorbance of said blood sample under a deoxygenated condition at a wavelength selected from 422-432 nm; (c) calculating a percent reduction in the second absorbance compared to the first absorbance; and (d) identifying the presence or absence of SCT or SCD in the subject based on the percent reduction.

In some embodiments, the present disclosure provides an in vitro method identifying the presence or absence of SCT or SCD in a subject, said method comprising: (a) mixing a first part of a blood sample from the subject with a first physiologically acceptable buffer comprising a detergent to obtain a first sample-buffer mixture; (b) measuring a first absorbance of the first sample-buffer mixture at a wavelength selected from 408-418 nm; (c) mixing a second part of said blood sample with a second physiologically acceptable buffer comprising a detergent and a reducing agent to obtain a second sample-buffer mixture; (d) measuring a second absorbance of the second sample-buffer mixture at a wavelength selected from 422-432 nm; (e) calculating a percent reduction in the second absorbance compared to the first absorbance; and (f) identifying the presence or absence of SCT or SCD in the subject based on the percent reduction.

The present disclosure also provides kits for performing the in vitro methods described herein. In some embodiments, a kit comprises: (a) a physiologically acceptable buffer; (b) a detergent; (c) a reducing agent; and (d) a document comprising instructions to perform the method and a table providing the ratio or the percent reduction to identify the presence or absence of HbS or HbC.

The present disclosure also provides a method for managing SCD in a subject, said method comprising: (a) measuring a first absorbance of a blood sample from the subject under a deoxygenated condition at a wavelength selected from 420-440 nm; (b) measuring a second absorbance of said blood sample under the deoxygenated condition at a wavelength selected from 545-565 nm; (c) calculating a ratio of the second absorbance to the first absorbance or a ratio of the first absorbance to the second absorbance; (d) identifying the presence or absence of SCD in the subject based on the ratio; and (e) if the subject has SCD, managing the SCD by administering an appropriate treatment or therapy to the subject.

The present disclosure also provides a method for managing SCD in a subject, said method comprising: (a) measuring a first absorbance of a blood sample from the subject under an oxygenated condition at a wavelength selected from 408-418 nm; (b) measuring a second absorbance of said blood sample under a deoxygenated condition at a wavelength selected from 422-432 nm; (c) calculating a percent reduction in the second absorbance compared to the first absorbance; (d) identifying the presence or absence of SCD in the subject based on the percent reduction; and (e) if the subject has SCD, managing the SCD by administering an appropriate treatment or therapy to the subject.

In some embodiments, the present disclosure provides a device for performing the in vitro methods described herein.

In some embodiments, the device comprises: (a) a light source for emitting light in the wavelength of 380-600 nm; (b) a detector for detecting the first absorbance and the second absorbance; and (c) a processor comprising instructions to calculate the ratio of the second absorbance to the first absorbance or a ratio of the first absorbance to the second absorbance.

BRIEF DESCRIPTION OF THE ACCOMPANYING FIGURES

FIG. 1 shows an exemplary absorbance spectrum of normal haemoglobin under oxygenated and deoxygenated conditions.

FIG. 2 shows an exemplary absorbance spectrum of control/normal blood, sickle cell trait blood, and sickle cell disease blood under oxygenated and deoxygenated conditions. Panel A shows the absorbance spectrum of control blood mixed with a buffer comprising detergent but no reducing agent (solid line) and a buffer comprising detergent and a reducing agent (dotted line). Panel B shows the absorbance spectrum of sickle cell trait blood mixed with a buffer comprising detergent but no reducing agent (solid line) and a buffer comprising detergent and a reducing agent (dotted line). Panel C shows the absorbance spectrum of sickle cell disease blood mixed with a buffer comprising detergent but no reducing agent (solid line) and a buffer comprising detergent and a reducing agent (dotted line).

DETAILED DESCRIPTION OF THE DISCLOSURE

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The use of the expression "at least" or "at least one" suggests the use of one or more elements or ingredients or quantities, as the use may be in the embodiment of the disclosure to achieve one or more of the desired objects or results. Throughout this specification, the word "comprise", or variations such as "comprises" or "comprising" or "containing" or "has" or "having", or "including but not limited to" wherever used, will be understood to imply the inclusion of a stated element, integer or step, or group of elements, integers or steps, but not the exclusion of any other element, integer or step, or group of elements, integers or steps.

Reference throughout this specification to "one embodiment" or "an embodiment" means that a particular feature, structure, or characteristic described in connection with the embodiment may be included in at least one embodiment of the present disclosure. Thus, the appearances of the phrases "in one embodiment" or "in an embodiment" in various places throughout this specification may not necessarily all refer to the same embodiment. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination.

The term "subject" or "patient" as used herein refers to a human.

The term "about" as used herein encompasses variations of +/−10% and more preferably +/−5%, as such variations are appropriate for practicing the present invention.

The terms "deoxygenated" and "hypoxic" are used interchangeably throughout this disclosure and refer to a condition where cells (e.g., RBCs) or cellular proteins (e.g., haemoglobin) experience inadequate levels of oxygen.

Figure 1:
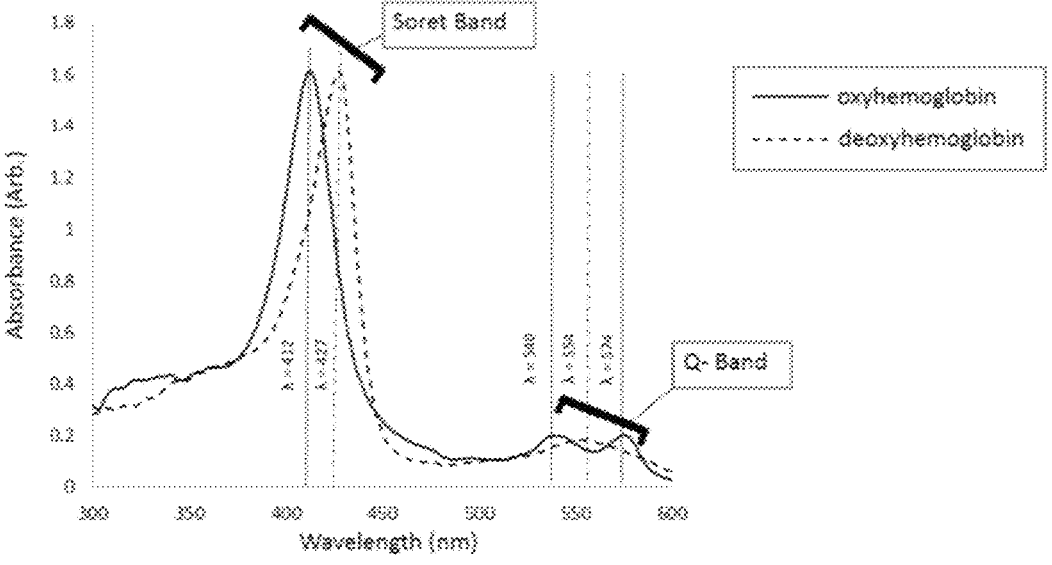

Haemoglobin (Hb) is made of four polypeptide chains ($\alpha 1$, $\alpha 2$, $\beta 1$, $\beta 2$), with each chain bound to a non-protein prosthetic group known as heme. Heme consists of an organic heterocyclic ring structure known as porphyrin with an iron atom held at the center. The metalloporphyrin structure of heme is responsible for the unique absorption spectrum of haemoglobin as shown in FIG. 1. Haemoglobin can exist as either oxyhaemoglobin or deoxyhaemoglobin depending on binding of oxygen to the iron atom of the metalloporphyrin ring. As shown in FIG. 1, the absorption spectrum of oxyhaemoglobin consists of two Q-bands (due to weak electronic transition from the ground state to first excited state) at about 574 nm ($\alpha$-band) and about 540 nm ($\beta$-band) and one Soret band (due to strong electronic transition from the ground state to second excited state) at about 412 nm. Under deoxygenated conditions due to conformational changes, the two Q-bands merge to form a single Q-band with a peak at about 554/555 nm and the Soret band experiences a redshift (peak shifts to ~427 nm).

Like normal hemoglobin (HbA), the absorption spectrum of HbS under oxygenated conditions shows one Soret band at about 412 nm and two Q bands at about 574 nm ($\alpha$-band) and about 540 nm ($\beta$-band). Further, similar to HbA, under deoxygenated conditions, HbS shows the redshift in the Soret band (peak shifts to ~427 nm). The present inventors, however, surprisingly found that, unlike HbA, the absorption spectrum of HbS under deoxygenated conditions shows a substantial decrease in absorption in the Soret band region. The present disclosure is the first to report this decrease in absorption in the Soret band region exhibited by HbS. The present inventors expect HbC also to show a similar decrease in absorption in the Soret band region.

Figure 2:
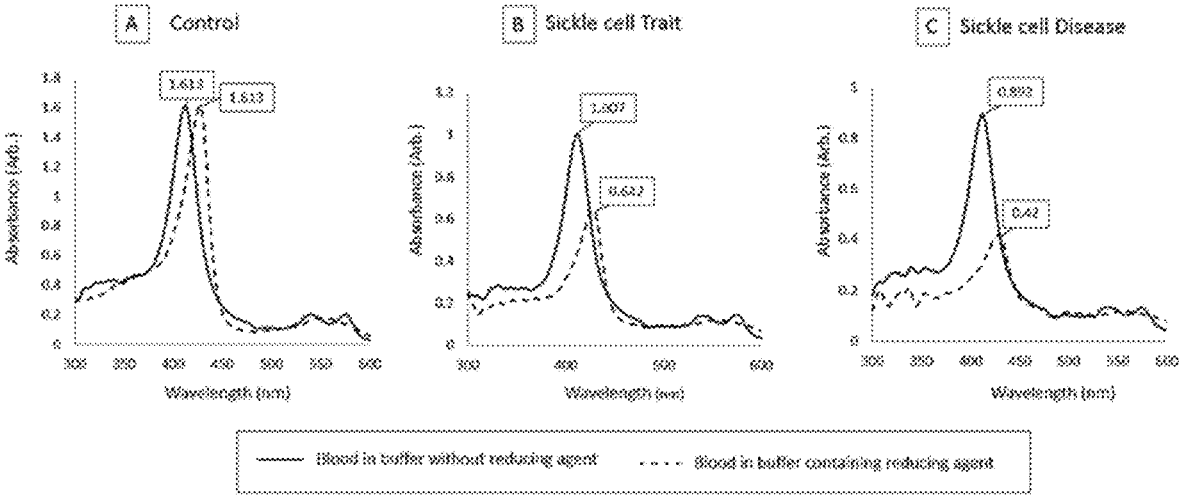

FIG. 2 shows the decrease in absorption by HbS in the Soret band region exhibited by HbS when exposed to deoxygenated conditions. In this figure, the solid line shows the absorption spectrum of HbA (normal haemoglobin) or HbS (abnormal haemoglobin found in SCD or SCT subjects) under oxygenated conditions and the dotted line shows the absorption spectrum of HbA or HbS under deoxygenated conditions. In this experiment, the oxygenated conditions comprised mixing the blood sample with a buffer comprising a detergent (Buffer 1) and the deoxygenated conditions comprised mixing the blood sample with a buffer comprising a detergent and a reducing agent (Buffer 2). The detergent lysed RBCs and released haemoglobin into the buffer solution (Buffer 1 and 2). The reducing agent created deoxygenated/hypoxic conditions in the buffer solution (Buffer 2).

FIG. 2, panel A shows an exemplary absorbance spectrum of normal blood (containing only HbA) when mixed with Buffer 1 (solid line, oxygenated conditions) and Buffer 2

(dotted line, deoxygenated conditions). A redshift is observed in the Soret band region under deoxygenated condition; however, the intensity of the Soret band absorption (molar extinction coefficient, c) under both oxygenated and deoxygenated conditions remains the same. FIG. 2, panel B shows an exemplary absorbance spectrum of a sickle cell trait blood (containing HbA and HbS) mixed with Buffer 1 (solid line, oxygenated conditions) and Buffer 2 (dotted line, deoxygenated conditions). A reduction in peak of the Soret band maxima (36.2%) is observed under the deoxygenated conditions (dotted line) when compared to oxygenated conditions (solid line). FIG. 2, panel C shows an exemplary absorbance spectrum of a sickle cell disease blood (containing only HbS) mixed with Buffer 1 (solid line, oxygenated conditions) and Buffer 2 (dotted line, deoxygenated conditions). In panel C, a further reduction in peak of the Soret band maxima (52.9%) is observed under the deoxygenated conditions (dotted line) compared to oxygenated conditions (solid line). Further, a higher reduction in peak at the Soret band maxima occurs under the deoxygenated conditions (dotted line) when compared to oxygenated conditions (solid line).

Without wishing to be bound by theory, it is hypothesized that the abnormal HbS haemoglobin polymerizes under the deoxygenated conditions rendered by the reducing agent. The so-formed HbS polymers are insoluble under high-salt conditions of the buffer, therefore, they precipitate out, causing the solution to become turbid. Other variants of hemoglobin (HbA, HbA2, HbF) are soluble in the buffer under these conditions. Thus, the buffer solution becomes turbid when blood from sickle cell trait or sickle cell disease is mixed with Buffer 2 (deoxygenated conditions). The density of the buffer keeps the HbS polymers suspended and prevents them from settling down. The absorbance spectrum of HbS in the presence of Buffer 2 (deoxygenated conditions) shows a reduction in the absorption maxima in the Soret band region as shown in FIGS. 2B and 2C. The present inventors are the first to report this decrease in absorption maxima in the Soret band region by HbS under deoxygenated conditions. Further, the inventors expect the absorption behavior of HbC to be similar to HbS.

The present invention employs this change in absorbance (molar extinction coefficient, c) in the Soret band region by HbS or HbC or as a method for identifying the presence or absence of HbS or HbC in a blood sample. Further, the inventors interestingly found that the extent of decrease in absorbance by HbS in the Soret band region under deoxygenated conditions can be employed to differentiate between homozygous (SCD) and heterozygous (SCT) conditions of sickle cell anemia. Accordingly, the present disclosure provides in vitro methods of identifying the presence or absence of HbS or HbC in a blood sample, in vitro methods of identifying the presence or absence of SCD or SCT in a subject, in vitro methods of determining the relative concentration of HbS or HbC in a blood sample, methods of managing SCD in a subject, and kits and devices thereof.

The in vitro methods of identifying the presence or absence of HbS or HbC in a blood sample or the in vitro methods of identifying the presence or absence of SCD or SCT in a subject as provided in the present disclosure broadly fall into two groups: (i) a method where the absorbance of a blood sample under deoxygenated conditions is measured in the Soret band region and the Q band region and a ratio of the two absorbance values is calculated to identify the presence or absence of HbS or HbC in the blood sample or to identify the presence or absence of SCD or SCT in a subject ("the ratio method"), and (ii) a method where the absorbance of a blood sample under oxygenated conditions and deoxygenated conditions is measured in the Soret band region and a percent reduction in the absorbance under deoxygenated conditions compared to oxygenated conditions is calculated to identify the presence or absence of HbS or HbC in the blood sample or to identify the presence or absence of SCD or SCT in a subject ("the percent reduction method").

The present disclosure also provides a kinetics method where the change in absorption maximum exhibited by a blood sample is measured over a period of time under deoxygenated conditions to determine whether the subject is healthy/normal or has SCT or SCD. Further, the present disclosure provides a method to determine the relative concentration of HbS or HbC in a blood sample where the decrease in absorbance measured in the percent reduction method is employed to determine the relative concentration of HbS or HbC.

The Ratio Method

In some embodiments, the present disclosure provides an in vitro method of identifying the presence or absence of haemoglobin S (HbS) or haemoglobin C (HbC) in a blood sample, said method comprising: (a) measuring a first absorbance of said blood sample under a deoxygenated condition at 420-440 nm; (b) measuring a second absorbance of said blood sample under the deoxygenated condition at 545-565 nm; (c) calculating a ratio of the second absorbance to the first absorbance or a ratio of the first absorbance to the second absorbance; and (d) identifying the presence or absence of HbS or HbC in said blood sample based on the ratio.

In this embodiment, the absorbance of a blood sample collected from a subject is measured under deoxygenated conditions at two different wavelengths—the Soret band region and the Q band region and a ratio of the two absorbance values is calculated to detect the presence or absence of HbS or HbC in the blood sample. In some embodiments, absorbance is measured using a spectrophotometer.

In some embodiments, a first absorbance of a blood sample is measured in the Soret band region at a wavelength selected from 420-440 nm under deoxygenated conditions and a second absorbance of the blood sample is measured in the Q band region at a wavelength selected from 545-565 nm under deoxygenated conditions. For example, in some embodiments, the first absorbance is measured in the Soret band region at a wavelength selected from 420-440 nm, 420-430 nm, 425-435 nm, 425-430 nm, or at 427 nm and the second absorbance is measured in the Q band region at a wavelength selected from 545-565 nm, 550-560 nm, 550-558 nm, or at 554 or 555 nm. To identify the presence or absence of HbS or HbC in the blood sample, a ratio of the first absorbance (measured at a wavelength from 420-440 nm) to the second absorbance (measured at a wavelength from 545-565 nm) or a ratio of the second absorbance to the first absorbance is calculated.

The deoxygenated condition is a condition in which RBCs or haemoglobin experiences inadequate oxygen levels. In some embodiments, the deoxygenated condition comprises mixing the subject's blood sample with a physiologically acceptable buffer comprising a detergent and a reducing agent to provide a sample-buffer mixture. The absorbance of this sample-buffer mixture is measured in the Soret band region and the Q band region.

Figure 3:
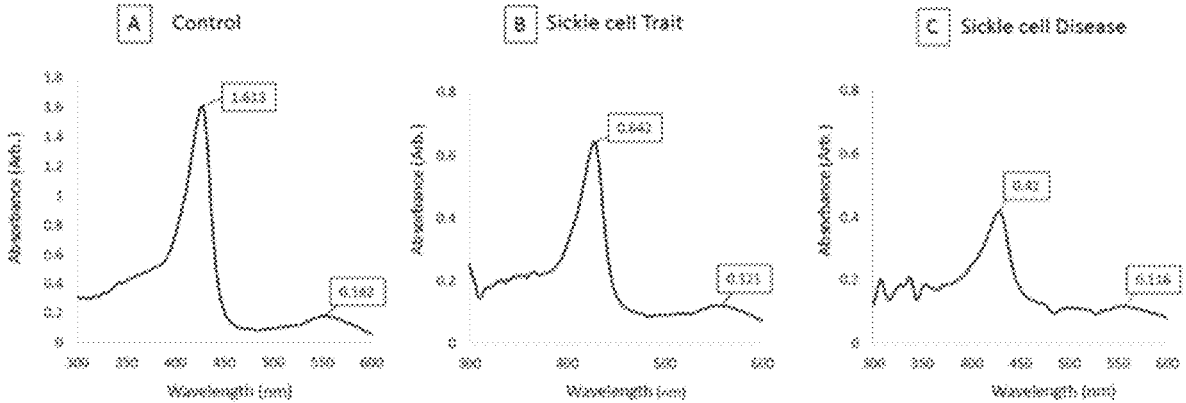
FIG. 3 shows an exemplary absorbance spectrum of control/normal blood (panel A), sickle cell trait blood (panel B), and sickle cell disease blood (panel C) mixed with a buffer comprising detergent and a reducing agent (deoxygenated conditions).

Accordingly, in some embodiments, the in vitro method of identifying the presence or absence of HbS or HbC in a blood sample comprises: (a) mixing said blood sample with a physiologically acceptable buffer comprising a detergent and a reducing agent to obtain a sample-buffer mixture; (b) measuring a first absorbance of the sample-buffer mixture at 420-440 nm; (c) measuring a second absorbance of the sample buffer mixture at 545-565 nm; (d) calculating a ratio of the second absorbance to the first absorbance or a ratio of the first absorbance to the second absorbance; and (e) identifying the presence or absence of HbS or HbC in said blood sample based on the ratio. FIG. 3 shows an exemplary absorbance pattern of control blood (panel A), sickle cell trait blood (panel B), and sickle cell disease blood (panel C) mixed with a buffer comprising detergent and a reducing agent.

In some embodiments, the sample-buffer mixture is incubated at room temperature for about 5 minutes to about 30 minutes prior to measuring the absorption in the Soret band region and the Q band region. In some embodiments, the sample-buffer mixture is incubated at room temperature for about 5 minutes to about 25 minutes, 5 minutes to about 20 minutes, 5 minutes to about 15 minutes, or 5 minutes to about 10 minutes. In some embodiments, the sample-buffer mixture is incubated at room temperature for about 5, 6, 7, 8, 9, 10, 11, 12, 13, 14, 15, 20, 21, 22, 23, 24, 25, 26, 27, 28, 29, or 30 minutes.

In some embodiments, the physiologically acceptable buffer employed in the methods of the present disclosure is selected from a phosphate buffer, a carbonate buffer, a citrate buffer, an acetate buffer, a HEPS buffer or a MOPS buffer. In some embodiments, a phosphate buffer having a concentration of about 1.5 M to 3.5 M is employed in the methods of the present disclosure. In some embodiments, a citrate buffer having a concentration of about 0.5 M to 2.5 M is employed in the methods of the present disclosure. In some embodiments, an acetate buffer having a concentration of about 1 M to 3.5 M is employed in the methods of the present disclosure. Methods to prepare these physiologically acceptable buffers are known in the art. Exemplary methods to prepare a phosphate buffer to perform the present methods are described in the Examples section.

In some embodiments, the physiologically acceptable buffer employed in the methods of the present disclosure is a phosphate buffer. In some embodiments, the phosphate buffer has a concentration of about 1.7 M to about 2.8 M, including values and ranges therebetween. For example, in some embodiments, the phosphate buffer has a concentration of about 1.7 M to about 2.8 M, about 1.7 M to about 2.7 M, about 1.7 M to about 2.6 M, about 1.7 M to about 2.5 M, about 1.7 M to about 2.4 M, about 1.7 M to about 2.3 M, about 1.7 M to about 2.2 M, about 1.7 M to about 2.1 M, about 1.7 M to about 2 M, about 1.8 M to about 2.8 M, about 1.8M to about 2.7 M, about 1.8 M to about 2.6 M, about 1.8 M to about 2.5 M, about 1.8 M to about 2.4 M, about 1.8 M to about 2.3 M, about 1.8 M to about 2.2 M, about 1.8 M to about 2.1 M, about 1.9 M to about 2.8 M, about 1.9 M to about 2.7 M, about 1.9 M to about 2.6 M, about 1.9 M to about 2.5 M, about 1.9 M to about 2.4 M, about 1.9 M to about 2.3 M, about 1.9 M to about 2.2 M, about 1.9 M to about 2.1 M, about 2 M to about 2.8 M, about 2 M to about 2.7 M, about 2 M to about 2.6 M, about 2 M to about 2.5 M, about 2 M to about 2.4 M, about 2 M to about 2.3 M, about 2 M to about 2.2 M, about 2 M to about 2.1 M, about 2.1 M to about 2.8 M, about 2.1 M to about 2.7 M, about 2.1 M to about 2.6 M, about 2.1 M to about 2.5 M, about 2.1 M to about 2.4 M, about 2.1 M to about 2.3 M, about 2.2 M to about 2.8 M, about 2.2 M to about 2.7 M, about 2.2 M to about 2.6 M, about 2.2 M to about 2.5 M, about 2.2 M to about 2.4 M, including values and ranges thereof. In an exemplary embodiment, the phosphate buffer has a concentration of about 2.0-2.5 M.

In some embodiments, the phosphate buffer has a molar concentration of about 1.7, 1.701, 1.702, 1.703, 1.704, 1.705, 1.706, 1.707, 1.708, 1.709, 1.71, 1.711, 1.712, 1.713, 1.714, 1.715, 1.716, 1.717, 1.718, 1.719, 1.72, 1.721, 1.722, 1.723, 1.724, 1.725, 1.726, 1.727, 1.728, 1.729, 1.73, 1.731, 1.732, 1.733, 1.734, 1.735, 1.736, 1.737, 1.738, 1.739, 1.74, 1.741, 1.742, 1.743, 1.744, 1.745, 1.746, 1.747, 1.748, 1.749, 1.75, 1.751, 1.752, 1.753, 1.754, 1.755, 1.756, 1.757, 1.758, 1.759, 1.76, 1.761, 1.762, 1.763, 1.764, 1.765, 1.766, 1.767, 1.768, 1.769, 1.77, 1.771, 1.772, 1.773, 1.774, 1.775, 1.776, 1.777, 1.778, 1.779, 1.78, 1.781, 1.782, 1.783, 1.784, 1.785, 1.786, 1.787, 1.788, 1.789, 1.79, 1.791, 1.792, 1.793, 1.794, 1.795, 1.796, 1.797, 1.798, 1.799, 1.8, 1.801, 1.802, 1.803, 1.804, 1.805, 1.806, 1.807, 1.808, 1.809, 1.81, 1.811, 1.812, 1.813, 1.814, 1.815, 1.816, 1.817, 1.818, 1.819, 1.82, 1.821, 1.822, 1.823, 1.824, 1.825, 1.826, 1.827, 1.828, 1.829, 1.83, 1.831, 1.832, 1.833, 1.834, 1.835, 1.836, 1.837, 1.838, 1.839, 1.84, 1.841, 1.842, 1.843, 1.844, 1.845, 1.846, 1.847, 1.848, 1.849, 1.85, 1.851, 1.852, 1.853, 1.854, 1.855, 1.856, 1.857, 1.858, 1.859, 1.86, 1.861, 1.862, 1.863, 1.864, 1.865, 1.866, 1.867, 1.868, 1.869, 1.87, 1.871, 1.872, 1.873, 1.874, 1.875, 1.876, 1.877, 1.878, 1.879, 1.88, 1.881, 1.882, 1.883, 1.884, 1.885, 1.886, 1.887, 1.888, 1.889, 1.89, 1.891, 1.892, 1.893, 1.894, 1.895, 1.896, 1.897, 1.898, 1.899, 1.9, 1.901, 1.902, 1.903, 1.904, 1.905, 1.906, 1.907, 1.908, 1.909, 1.91, 1.911, 1.912, 1.913, 1.914, 1.915, 1.916, 1.917, 1.918, 1.919, 1.92, 1.921, 1.922, 1.923, 1.924, 1.925, 1.926, 1.927, 1.928, 1.929, 1.93, 1.931, 1.932, 1.933, 1.934, 1.935, 1.936, 1.937, 1.938, 1.939, 1.94, 1.941, 1.942, 1.943, 1.944, 1.945, 1.946, 1.947, 1.948, 1.949, 1.95, 1.951, 1.952, 1.953, 1.954, 1.955, 1.956, 1.957, 1.958, 1.959, 1.96, 1.961, 1.962, 1.963, 1.964, 1.965, 1.966, 1.967, 1.968, 1.969, 1.97, 1.971, 1.972, 1.973, 1.974, 1.975, 1.976, 1.977, 1.978, 1.979, 1.98, 1.981, 1.982, 1.983, 1.984, 1.985, 1.986, 1.987, 1.988, 1.989, 1.99, 1.991, 1.992, 1.993, 1.994, 1.995, 1.996, 1.997, 1.998, 1.999, 2.0, 2.001, 2.002, 2.003, 2.004, 2.005, 2.006, 2.007, 2.008, 2.009, 2.01, 2.011, 2.012, 2.013, 2.014, 2.015, 2.016, 2.017, 2.018, 2.019, 2.02, 2.021, 2.022, 2.023, 2.024, 2.025, 2.026, 2.027, 2.028, 2.029, 2.03, 2.031, 2.032, 2.033, 2.034, 2.035, 2.036, 2.037, 2.038, 2.039, 2.04, 2.041, 2.042, 2.043, 2.044, 2.045, 2.046, 2.047, 2.048, 2.049, 2.05, 2.051, 2.052, 2.053, 2.054, 2.055, 2.056, 2.057, 2.058, 2.059, 2.06, 2.061, 2.062, 2.063, 2.064, 2.065, 2.066, 2.067, 2.068, 2.069, 2.07, 2.071, 2.072, 2.073, 2.074, 2.075, 2.076, 2.077, 2.078, 2.079, 2.08, 2.081, 2.082, 2.083, 2.084, 2.085, 2.086, 2.087, 2.088, 2.089, 2.09, 2.091, 2.092, 2.093, 2.094, 2.095, 2.096, 2.097, 2.098, 2.099, 2.1, 2.101, 2.102, 2.103, 2.104, 2.105, 2.106, 2.107, 2.108, 2.109, 2.11, 2.111, 2.112, 2.113, 2.114, 2.115, 2.116, 2.117, 2.118, 2.119, 2.12, 2.121, 2.122, 2.123, 2.124, 2.125, 2.126, 2.127, 2.128, 2.129, 2.13, 2.131, 2.132, 2.133, 2.134, 2.135, 2.136, 2.137, 2.138, 2.139, 2.14, 2.141, 2.142, 2.143, 2.144, 2.145, 2.146, 2.147, 2.148, 2.149, 2.15, 2.151, 2.152, 2.153, 2.154, 2.155, 2.156, 2.157, 2.158, 2.159, 2.16, 2.161, 2.162, 2.163, 2.164, 2.165, 2.166, 2.167, 2.168, 2.169, 2.17, 2.171, 2.172, 2.173, 2.174, 2.175, 2.176, 2.177, 2.178, 2.179, 2.18, 2.181, 2.182, 2.183, 2.184, 2.185, 2.186, 2.187, 2.188, 2.189, 2.19, 2.191, 2.192, 2.193, 2.194, 2.195, 2.196, 2.197, 2.198, 2.199, 2.2, 2.201, 2.202, 2.203, 2.204, 2.205, 2.206, 2.207, 2.208, 2.209, 2.21, 2.211, 2.212, 2.213, 2.214, 2.215, 2.216, 2.217, 2.218, 2.219, 2.22, 2.221, 2.222, 2.223, 2.224, 2.225, 2.226, 2.227, 2.228, 2.229, 2.23, 2.231, 2.232, 2.233, 2.234, 2.235, 2.236, 2.237, 2.238, 2.239, 2.24, 2.241, 2.242, 2.243, 2.244, 2.245, 2.246, 2.247, 2.248, 2.249, 2.25, 2.251, 2.252, 2.253, 2.254, 2.255, 2.256, 2.257, 2.258, 2.259, 2.26, 2.261, 2.262, 2.263, 2.264, 2.265, 2.266, 2.267, 2.268, 2.269, 2.27, 2.271, 2.272, 2.273, 2.274, 2.275, 2.276, 2.277, 2.278, 2.279, 2.28, 2.281, 2.282, 2.283, 2.284, 2.285, 2.286, 2.287, 2.288, 2.289, 2.29, 2.291, 2.292, 2.293, 2.294, 2.295, 2.296, 2.297, 2.298, 2.299, 2.3, 2.301, 2.302, 2.303, 2.304, 2.305, 2.306, 2.307, 2.308, 2.309, 2.31, 2.311, 2.312, 2.313, 2.314, 2.315, 2.316, 2.317, 2.318, 2.319, 2.32, 2.321, 2.322, 2.323, 2.324, 2.325, 2.326, 2.327, 2.328, 2.329, 2.33, 2.331, 2.332, 2.333, 2.334, 2.335, 2.336, 2.337, 2.338, 2.339, 2.34, 2.341, 2.342, 2.343, 2.344, 2.345, 2.346, 2.347, 2.348, 2.349, 2.35, 2.351, 2.352, 2.353, 2.354, 2.355, 2.356, 2.357, 2.358, 2.359, 2.36, 2.361, 2.362, 2.363, 2.364, 2.365, 2.366, 2.367, 2.368, 2.369, 2.37, 2.371, 2.372, 2.373, 2.374, 2.375, 2.376, 2.377, 2.378, 2.379, 2.38, 2.381, 2.382, 2.383, 2.384, 2.385, 2.386, 2.387, 2.388, 2.389, 2.39, 2.391, 2.392, 2.393, 2.394, 2.395, 2.396, 2.397, 2.398, 2.399, 2.4, 2.401, 2.402, 2.403, 2.404, 2.405, 2.406, 2.407, 2.408, 2.409, 2.41, 2.411, 2.412, 2.413, 2.414, 2.415, 2.416, 2.417, 2.418, 2.419, 2.42, 2.421, 2.422, 2.423, 2.424, 2.425, 2.426, 2.427, 2.428, 2.429, 2.43, 2.431, 2.432, 2.433, 2.434, 2.435, 2.436, 2.437, 2.438, 2.439, 2.44, 2.441, 2.442, 2.443, 2.444, 2.445, 2.446, 2.447, 2.448, 2.449, 2.45, 2.451, 2.452, 2.453, 2.454, 2.455, 2.456, 2.457, 2.458, 2.459, 2.46, 2.461, 2.462, 2.463, 2.464, 2.465, 2.466, 2.467, 2.468, 2.469, 2.47, 2.471, 2.472, 2.473, 2.474, 2.475, 2.476, 2.477, 2.478, 2.479, 2.48, 2.481, 2.482, 2.483, 2.484, 2.485, 2.486, 2.487, 2.488, 2.489, 2.49, 2.491, 2.492, 2.493, 2.494, 2.495, 2.496, 2.497, 2.498, 2.499, 2.5, 2.501, 2.502, 2.503, 2.504, 2.505, 2.506, 2.507, 2.508, 2.509, 2.51, 2.511, 2.512, 2.513, 2.514, 2.515, 2.516, 2.517, 2.518, 2.519, 2.52, 2.521, 2.522, 2.523, 2.524, 2.525, 2.526, 2.527, 2.528, 2.529, 2.53, 2.531, 2.532, 2.533, 2.534, 2.535, 2.536, 2.537, 2.538, 2.539, 2.54, 2.541, 2.542, 2.543, 2.544, 2.545, 2.546, 2.547, 2.548, 2.549, 2.55, 2.551, 2.552, 2.553, 2.554, 2.555, 2.556, 2.557, 2.558, 2.559, 2.56, 2.561, 2.562, 2.563, 2.564, 2.565, 2.566, 2.567, 2.568, 2.569, 2.57, 2.571, 2.572, 2.573, 2.574, 2.575, 2.576, 2.577, 2.578, 2.579, 2.58, 2.581, 2.582, 2.583, 2.584, 2.585, 2.586, 2.587, 2.588, 2.589, 2.59, 2.591, 2.592, 2.593, 2.594, 2.595, 2.596, 2.597, 2.598, 2.599, or 2.6, including values and ranges therebetween.

In some embodiments, the detergent added to the physiologically acceptable buffer to lyse RBCs is selected from saponin, SDS (sodium dodecyl sulfate), SLS (sodium lauryl sulfate), and a polysorbate (e.g. TWEEN® 20). In some embodiments, the detergent is added at a concentration of about 0.1-2%, about 0.2-2%, about 0.4-2%, about 0.4-1.5%, about 0.4-1%, about 0.5-2%, about 0.75-2%, about 0.8-2%, about 1-2%, about 1.25-2%, or about 1.5-2%, by weight of the buffer, including values and ranges therebetween. In some embodiments, the detergent is added at a concentration of about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2%, by weight of the buffer.

In some embodiments, the reducing agent added to the physiologically acceptable buffer to induce deoxygenated/hypoxic conditions is selected from sodium metabisulfite, sodium dithionate, disodium disulphate, sulfate tetrasodium, sodium dithionate hydrate, sodium trithionate. In some embodiments, the reducing agent is added at a concentration of about 0.5-6%, 0.5-5.5%, 0.5-5%, 0.5-4.5%, 0.5-4%, 0.5-3%, 0.5-2.5%, 1-6%, 1.5.5%, 1-5%, 1-4.5%, 1-4%, 1-3.5%, 1-3%, 1.5-6%, 1.5-5.5%, 1.5-5%, 1.5-4.5%, 1.5-4%, 1.5-3.5%, 2-6%, 2-5%, 2-4%, 3-6%, 3-5%, or 4-6%, by weight of the buffer, including values and ranges therebetween. In some embodiments, the reducing agent is added at a concentration of about 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, 5%, 5.1%, 5.2%, 5.3%, 5.4%, 5.5%, 5.6%, 5.7%, 5.8%, 5.9%, or 6% by weight of the buffer.

In some embodiments, the in vitro method of identifying the presence or absence of HbS or HbC in a blood sample comprises: (a) mixing said blood sample with a 1.7-2.8 M phosphate buffer comprising saponin and sodium metabisulfite to obtain a sample-buffer mixture; (b) measuring a first absorbance of the sample-buffer mixture at 425-430 nm; (c) measuring a second absorbance of the sample-buffer mixture at 550-560 nm; (d) calculating a ratio of the second absorbance to the first absorbance or a ratio of the first absorbance to the second absorbance; and (e) identifying the presence or absence of HbS or HbC in said blood sample based on the ratio.

In some embodiments, the in vitro method of identifying the presence or absence of HbS or HbC in a blood sample comprises: (a) mixing said blood sample with a 2.0-2.5 M phosphate buffer comprising saponin and sodium metabisulfite to obtain a sample-buffer mixture; (b) measuring a first absorbance of the sample-buffer mixture at 425-430 nm; (c) measuring a second absorbance of the sample-buffer mixture at 550-560 nm; (d) calculating a ratio of the second absorbance to the first absorbance or a ratio of the first absorbance to the second absorbance; and (e) identifying the presence or absence of HbS or HbC in said blood sample based on the ratio.

In some embodiments, the in vitro method of identifying the presence or absence of HbS or HbC in a blood sample comprises: (a) mixing said blood sample with a 1.7-2.8 M phosphate buffer comprising saponin and sodium metabisulfite to obtain a sample-buffer mixture; (b) measuring a first absorbance of the sample-buffer mixture at 427 nm; (c) measuring a second absorbance of the sample-buffer mixture at 554 nm or 555 nm; (d) calculating a ratio of the second absorbance to the first absorbance or a ratio of the first absorbance to the second absorbance; and (e) identifying the presence or absence of HbS or HbC in said blood sample based on the ratio.

In some embodiments, the in vitro method of identifying the presence or absence of HbS or HbC in a blood sample comprises: (a) mixing said blood sample with a 2.0-2.5 M phosphate buffer comprising saponin and sodium metabisulfite to obtain a sample-buffer mixture; (b) measuring a first absorbance of the sample-buffer mixture at 427 nm; (c) measuring a second absorbance of the sample-buffer mixture at 554 nm or 555 nm; (d) calculating a ratio of the second absorbance to the first absorbance or a ratio of the first absorbance to the second absorbance; and (e) identifying the presence or absence of HbS or HbC in said blood sample based on the ratio.

The inventors have found that when a blood sample is mixed with 2.365 M phosphate buffer comprising saponin and sodium metabisulfite (each added to a final concentration of about 2% by weight) and incubated at room temperature for about 5-30 minutes, the ratio of the second absorbance ($A_{555}$) to the first absorbance ($A_{427}$) of less than 0.16 indicates the absence of HbS (i.e., the blood sample is from a healthy subject) whereas the $A_{555}/A_{427}$ ratio of 0.16 or higher indicates the presence of HbS (i.e., the blood sample is from a subject having SCT or SCD). This is shown in Table 1A below:

TABLE 1A

| $A_{555}/A_{427}$ ratio and the presence or absence of HbS (blood sample mixed with 2.365M phosphate buffer comprising saponin and sodium metabisulfite, added to a final concentration of about 0.4% and about 2% by weight, respectively, incubated at room temperature for about 5-30 minutes, and the absorbance measured at 427 nm and 555 nm) | |
| --- | --- |
| $A_{555}/A_{427}$ | HbS |
| <0.16 | Absent |
| ≥0.16 | Present |

Further, the inventors have found that under these conditions, when the $A_{555}/A_{427}$ ratio is between 0.16 to 0.24, the blood sample is from a subject having SCT (i.e., heterozygous HbS with HbA/HbF) and when the $A_{555}/A_{427}$ ratio is greater than 0.24, the blood sample is from a subject having SCD (homozygous HbSS). This is shown in Table 1B below:

TABLE 1B

| The $A_{555}/A_{427}$ ratio and the identification of SCT/SCD (blood sample mixed with 2.365M phosphate buffer comprising saponin and sodium metabisulfite, added to a final concentration of about 0.4% and about 2% by weight, respectively, incubated at room temperature for about 5-30 minutes, and the absorbance measured at 427 nm and 555 nm) | |
| --- | --- |
| $A_{555}/A_{427}$ | Test Prediction |
| 0.16-0.24 | Sickle cell trait (Heterozygous HbS with HbA/HbF) |
| >0.24 | Sickle cell disease (Homozygous HbSS) |

Under the same mixing and incubation conditions (i.e., blood sample mixed with 2.365 M phosphate buffer comprising saponin and sodium metabisulfite, each added to a final concentration of 2% by weight, and incubated at room temperature for about 5-30 minutes), threshold values for the ratio of the first absorbance to the second absorbance $(A_{427}/A_{555})$ to identify the presence or absence of HbS are shown in Table 2A below:

TABLE 2A

| The $A_{427}/A_{555}$ ratio and the presence or absence of HbS (blood sample mixed with 2.365M phosphate buffer comprising saponin and sodium metabisulfite, added to a final concentration of about 0.4% and about 2% by weight, respectively, incubated at room temperature for about 5-30 minutes, and the absorbance measured at 427 nm and 555 nm) | |
| --- | --- |
| $A_{427}/A_{555}$ | HbS |
| >6 | Absent |
| ≤6 | Present |

Further, the inventors have found that under these conditions, when the $A_{427}/A_{555}$ ratio is between 4 to 6, the blood sample is from a subject having SCT (i.e., heterozygous HbS with HbA/HbF) and when the $A_{427}/A_{555}$ ratio is less than 4, the blood sample is from a subject having SCD (homozygous HbSS). This is shown in Table 2B below:

TABLE 2B

| The $A_{427}/A_{555}$ ratio and the identification of SCT/SCD (blood sample mixed with 2.365M phosphate buffer comprising saponin and sodium metabisulfite, added to a final concentration of about 0.4% and about 2% by weight, respectively, incubated at room temperature for about 5-30 minutes, and the absorbance measured at 427 nm and 555 nm) | |
| --- | --- |
| $A_{427}/A_{555}$ | Test Prediction |
| 4-6 | Sickle cell trait (Heterozygous HbS with HbA/HbF) |
| <4 | Sickle cell disease (Homozygous HbSS) |

When a blood sample is mixed with 2.083 M phosphate buffer comprising saponin and sodium metabisulfite, added to a final concentration of about 0.4% and about 2% by weight, respectively, and incubated at room temperature for about 5-30 minutes, the ratio of the second absorbance $(A_{555})$ to the first absorbance $(A_{427})$ of less than 0.11 indicates the absence of HbS (i.e., the blood sample is from a healthy subject) whereas the $A_{555}/A_{427}$ ratio of 0.11 or higher indicates the presence of HbS (i.e., the blood sample is from a subject having SCT or SCD). This is shown in Table 3A below.

TABLE 3A

| The $A_{555}/A_{427}$ ratio and the presence or absence of HbS (blood sample mixed with 2.083M phosphate buffer comprising saponin and sodium metabisulfite, added to a final concentration of about 0.4% and about 2% by weight, respectively, incubated at room temperature for about 5-30 minutes, and the absorbance measured at 427 nm and 555 nm) | |
| --- | --- |
| $A_{555}/A_{427}$ | HbS |
| <0.11 | Absent |
| ≥0.11 | Present |

Further, the inventors have found that under these conditions, when the $A_{555}/A_{427}$ ratio is between 0.11 to 0.15, the blood sample is from a subject having SCT (i.e., heterozygous HbS with HbA/HbF) and when the $A_{555}/A_{427}$ ratio is greater than 0.15, the blood sample is from a subject having SCD (homozygous HbSS). This is shown in Table 3B below:

TABLE 3B

| The $A_{555}/A_{427}$ ratio and the identification of SCT/SCD (blood sample mixed with 2.083M phosphate buffer comprising saponin and sodium metabisulfite, added to a final concentration of about 0.4% and about 2% by weight, respectively, incubated at room temperature for about 5-30 minutes, and the absorbance measured at 427 nm and 555 nm) | |
| --- | --- |
| $A_{555}/A_{427}$ | Test Prediction |
| 0.11-0.15 | Sickle cell trait (Heterozygous HbS with HbA/HbF) |
| >0.15 | Sickle cell disease (Homozygous HbSS) |

Under the same mixing and incubation conditions (i.e., blood sample mixed with 2.083 M phosphate buffer comprising saponin and sodium metabisulfite, added to a final concentration of about 0.4% and about 2% by weight, respectively, and incubated at room temperature for about 5-30 minutes), threshold values for the ratio of the first absorbance to the second absorbance $(A_{427}/A_{555})$ to identify the presence or absence of HbS are shown in Table 4A below:

TABLE 4A

The $A_{427}/A_{555}$ ratio and the presence or absence of HbS (blood sample mixed with 2.083M phosphate buffer comprising saponin and sodium metabisulfite, added to a final concentration of about 0.4% and about 2% by weight, respectively, incubated at room temperature for about 5-30 minutes, and the absorbance measured at 427 nm and 555 nm)

| $A_{427}/A_{555}$ | HbS |
|---|---|
| >8 | Absent |
| ≤8 | Present |

Further, the inventors have found that under these conditions, when the $A_{427}/A_{555}$ ratio is between 6.5 to 8, the blood sample is from a subject having SCT (i.e., heterozygous HbS with HbA/HbF) and when the $A_{427}/A_{555}$ ratio is less than 6.5, the blood sample is from a subject having SCD (homozygous HbSS). This is shown in Table 4B below:

TABLE 4B

The $A_{427}/A_{555}$ ratio and the identification of SCT/SCD (blood sample mixed with 2.083M phosphate buffer comprising saponin and sodium metabisulfite, added to a final concentration of about 0.4% and about 2% by weight, respectively, incubated at room temperature for about 5-30 minutes, and the absorbance measured at 427 nm and 555 nm)

| $A_{427}/A_{555}$ | Test Prediction |
|---|---|
| 6.5-8 | Sickle cell trait (Heterozygous HbS with HbA/HbF) |
| <6.5 | Sickle cell disease (Homozygous HbSS) |

Figure 4:
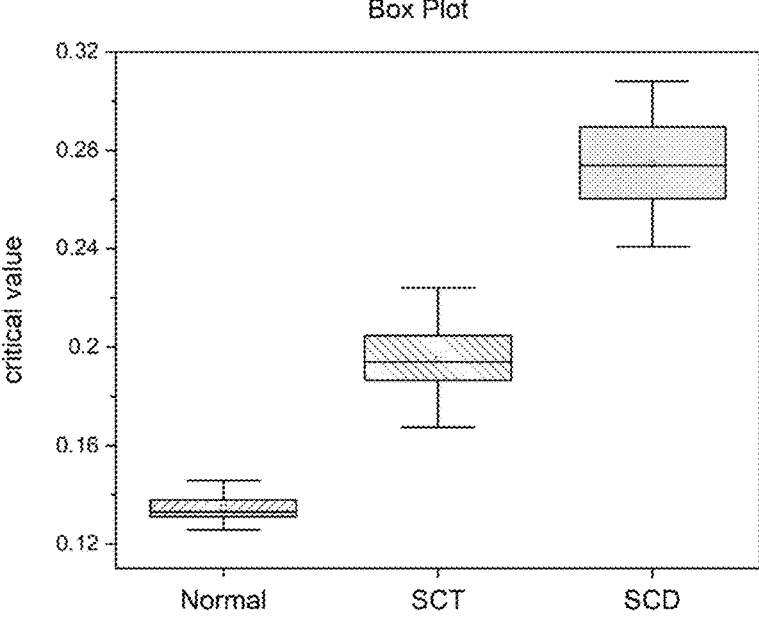
FIG. 4 shows an exemplary box plot depicting the distribution of threshold ratio values for control/normal blood, sickle cell trait (SCT) blood, and sickle cell disease (SCD) blood.

The inventors have found that, when a blood sample is treated under the same buffer and incubation conditions, the distribution of threshold values for the ratio of the second absorbance to the first absorbance (e.g., $A_{555}/A_{427}$) or the ratio of the first absorbance to the second absorbance (e.g., $A_{427}/A_{555}$) for the three groups of subjects—control/healthy, SCT, and SCD—is very tight; i.e., even after subject to subject variations, there is a clear demarcation in threshold ratio values based on which one can accurately identify whether the subject is healthy or has SCT (sickle cell trait) or SCD (sickle cell disease). An exemplary distribution of threshold ratio values that distinguish between normal, SCT, and SCD conditions, when a blood sample is treated with 2.365 M phosphate buffer comprising saponin and sodium metabisulfite, added to a final concentration of about 0.4% and about 2% by weight, respectively, incubated at room temperature for about 5-30 minutes, and the absorbance measured at 427 nm and 554 nm, is shown in FIG. 4.

Accordingly, the present disclosure provides in vitro methods of identifying the presence or absence of SCT or SCD in a subject based on the ratio values.

In some embodiments, an in vitro method of identifying the presence or absence of SCT or SCD in a subject comprises: (a) measuring a first absorbance of a blood sample from the subject under a deoxygenated condition at 420-440 nm; (b) measuring a second absorbance of said blood sample under the deoxygenated condition at 545-565 nm; (c) calculating a ratio of the second absorbance to the first absorbance or a ratio of the first absorbance to the second absorbance; and (d) identifying the presence or absence of SCT or SCD in the subject based on the ratio.

In some embodiments, deoxygenated conditions are as described above. Accordingly, in some embodiments, an in vitro method of identifying the presence or absence of SCT or SCD in a subject comprises: (a) mixing a blood sample from the subject with a physiologically acceptable buffer comprising a detergent and a reducing agent to obtain a sample-buffer mixture; (b) measuring a first absorbance of the sample-buffer mixture at 420-440 nm; (c) measuring a second absorbance of the sample buffer mixture at 545-565 nm; (d) calculating a ratio of the second absorbance to the first absorbance or a ratio of the first absorbance to the second absorbance; and (e) identifying the presence or absence of SCT or SCD in the subject based on the ratio.

The physiologically acceptable buffer, the detergent, the reducing agent, and their respective concentrations are as described herein.

In some embodiments, the in vitro method of identifying the presence or absence of SCT or SCD in a subject comprises: (a) mixing a blood sample from the subject with a 1.7-2.8 M phosphate buffer comprising saponin and sodium metabisulfite to obtain a sample-buffer mixture; (b) measuring a first absorbance of the sample-buffer mixture at 425-430 nm; (c) measuring a second absorbance of the sample-buffer mixture at 550-560 nm; (d) calculating a ratio of the second absorbance to the first absorbance or a ratio of the first absorbance to the second absorbance; and (e) identifying the presence or absence of SCT or SCD in the subject based on the ratio.

In some embodiments, the in vitro method of identifying the presence or absence of SCT or SCD in a subject comprises: (a) mixing a blood sample from the subject with a 2.0-2.5 M phosphate buffer comprising saponin and sodium metabisulfite to obtain a sample-buffer mixture; (b) measuring a first absorbance of the sample-buffer mixture at 425-430 nm; (c) measuring a second absorbance of the sample-buffer mixture at 550-560 nm; (d) calculating a ratio of the second absorbance to the first absorbance or a ratio of the first absorbance to the second absorbance; and (e) identifying the presence or absence of SCT or SCD in the subject based on the ratio.

In some embodiments, the in vitro method of identifying the presence or absence of SCT or SCD in a subject comprises: (a) mixing a blood sample from the subject with a 1.7-2.8 M phosphate buffer comprising saponin and sodium metabisulfite to obtain a sample-buffer mixture; (b) measuring a first absorbance of the sample-buffer mixture at 427 nm; (c) measuring a second absorbance of the sample-buffer mixture at 554 nm or 555 nm; (d) calculating a ratio of the second absorbance to the first absorbance or a ratio of the first absorbance to the second absorbance; and (e) identifying the presence or absence of SCT or SCD in the subject based on the ratio.

In some embodiments, the in vitro method of identifying the presence or absence of SCT or SCD in a subject comprises: (a) mixing a blood sample from the subject with a 2.0-2.5 M phosphate buffer comprising saponin and sodium metabisulfite to obtain a sample-buffer mixture; (b) measuring a first absorbance of the sample-buffer mixture at 427 nm; (c) measuring a second absorbance of the sample-buffer mixture at 554 nm or 555 nm; (d) calculating a ratio of the second absorbance to the first absorbance or a ratio of the first absorbance to the second absorbance; and (e) identifying the presence or absence of SCT or SCD in the subject based on the ratio.

The Percent Reduction Method

In some embodiments, the present disclosure provides an in vitro method of identifying the presence or absence of haemoglobin S (HbS) or haemoglobin C (HbC) in a blood sample, said method comprising: (a) measuring a first absorbance of said blood sample under an oxygenated condition at 400-421 nm; (b) measuring a second absorbance of said blood sample under a deoxygenated condition at 422-440 nm; (c) calculating a percent reduction in the second absorbance compared to the first absorbance; and (d) identifying the presence or absence of HbS or HbC in said blood sample based on the percent reduction.

In this embodiment, the absorbance of a blood sample collected from a subject is measured under oxygenated conditions at a wavelength selected from 400-421 nm (first absorbance) and the absorbance of the blood sample is measured under deoxygenated conditions at a wavelength selected from 422-440 nm (second absorbance). A percent reduction in the second absorbance (deoxygenated conditions) compared to the first absorbance (oxygenated conditions) is calculated to detect the presence or absence of HbS or HbC in the blood sample. In some embodiments, the absorbance is measured using a spectrophotometer.

As discussed in the present disclosure, the absorption spectrum of haemoglobin under oxygenated conditions shows the Soret band at about 412 nm. Under deoxygenated conditions, due to conformational changes in haemoglobin, the Soret band experiences a redshift (peak shifts to about 427 nm). Interestingly, haemoglobin from SCT or SCD subjects under deoxygenated conditions shows the redshift to about 427 nm but also shows a substantial decrease in absorption. The percent reduction method measures this decrease in absorption to identify the presence or absence of HbS or HbC. In this method, the absorbance of a blood sample under oxygenated conditions is measured in the 400-421 nm region (first absorbance), the absorbance of the blood sample under deoxygenated conditions is measured in the 422-440 nm region (second absorbance) and a percent decrease in second absorbance compared to the first absorbance is measured to identify the presence or absence of HbS or HbC in the blood sample.

In some embodiments, the oxygenated conditions comprise mixing the subject's blood sample with a physiologically acceptable buffer comprising a detergent, but not a reducing agent, to provide a first sample-buffer mixture. The physiologically acceptable buffer, the detergent, and their respective concentrations are as described herein.

In some embodiments, the deoxygenated conditions comprise mixing the subject's blood sample with a physiologically acceptable buffer comprising a detergent and a reducing agent to provide a second sample-buffer mixture. The physiologically acceptable buffer, the detergent, the reducing agent, and their respective concentrations are as described herein.

The absorbance of the first sample-buffer mixture (first absorbance) is measured at a wavelength selected from 400-421 nm, 410-420 nm, 408-418 nm, 410-415 nm, 412 nm, or 415 nm and the absorbance of the second sample-buffer mixture (second absorbance) is measured at a wavelength selected from 422-440 nm, 422-432 nm, 425-440 nm, 425-430 nm, 425 nm, or 427 nm. A percent decrease in the second absorbance compared to the first absorbance is calculated.

Accordingly, in some embodiments, the in vitro method of identifying the presence or absence of haemoglobin S (HbS) or haemoglobin C (HbC) in a blood sample, comprises: (a) mixing a first part of said blood sample with a first physiologically acceptable buffer comprising a detergent to obtain a first sample-buffer mixture; (b) measuring a first absorbance of the first sample-buffer mixture at 400-421 nm; (c) mixing a second part of said blood sample with a second physiologically acceptable buffer comprising a detergent and a reducing agent to obtain a second sample-buffer mixture; (d) measuring a second absorbance of the second sample-buffer mixture at 422-440 nm; (e) calculating a percent reduction in the second absorbance compared to the first absorbance; and (f) identifying the presence or absence of HbS or HbC in said blood sample based on the percent reduction.

In some embodiments, the first and the second sample-buffer mixtures are incubated at room temperature for about 5 minutes to about 30 minutes prior to measuring their absorption. In some embodiments, the sample-buffer mixture is incubated at room temperature for about 5 minutes to about 25 minutes, about 5 minutes to about 20 minutes, about 5 minutes to about 15 minutes, or about 5 minutes to about 10 minutes. In some embodiments, the sample-buffer mixture is incubated at room temperature for about 5, 6, 7, 8, 9, 10, 11, 12, 13, 14, 15, 20, 21, 22, 23, 24, 25, 26, 27, 28, 29, or 30 minutes.

In some embodiments, the in vitro method of identifying the presence or absence of HbS or HbC in a blood sample comprises: (a) mixing a first part of said blood sample with a 1.7-2.8 M phosphate buffer comprising saponin to obtain a first sample-buffer mixture; (b) measuring a first absorbance of the first sample-buffer mixture at a wavelength selected from 400-421 nm, 410-420 nm, 408-418 nm, 410-415 nm, 412 nm, or 415 nm; (c) mixing a second part of said blood sample with a 1.7-2.8 M phosphate buffer comprising saponin and sodium metabisulfite to obtain a second sample-buffer mixture; (d) measuring a second absorbance of the second sample-buffer mixture at a wavelength selected from 422-440 nm, 422-432 nm, 425-435 nm, 425-430 nm, 425 nm, or 427 nm; (e) calculating a percent reduction in the second absorbance compared to the first absorbance; and (f) identifying the presence or absence of HbS or HbC in said blood sample based on the percent reduction.

In some embodiments, the in vitro method of identifying the presence or absence of HbS or HbC in a blood sample comprises: (a) mixing a first part of said blood sample with 2.49 M phosphate buffer comprising saponin to obtain a first sample-buffer mixture; (b) measuring a first absorbance of the first sample-buffer mixture at a wavelength selected from 400-421 nm, 410-420 nm, 408-418 nm, 410-415 nm, 412 nm, or 415 nm; (c) mixing a second part of said blood sample with 2.49 M phosphate buffer comprising saponin and sodium metabisulfite to obtain a second sample-buffer mixture; (d) measuring a second absorbance of the second sample-buffer mixture at a wavelength selected from 422-440 nm, 422-432 nm, 425-435 nm, 425-430 nm, 425 nm, or 427 nm; (e) calculating a percent reduction in the second absorbance compared to the first absorbance; and (f) identifying the presence or absence of HbS or HbC in said blood sample based on the percent reduction.

The inventors have found that since the absorption spectrum of normal haemoglobin only shows the red shift, but does not show a decrease in absorption under deoxygenated conditions compared to oxygenated conditions, a blood sample containing only normal haemoglobin shows less than 5% reduction in the second absorbance value measured at a wavelength selected from 422-440 nm, 422-432 nm, 425-435 nm, 425-430 nm, 425 nm, or 427 nm compared to the first absorption value measured at a wavelength selected from 400-421 nm, 410-420 nm, 408-418 nm, 410-415 nm, 412 nm, or 415 nm. On the other hand, the inventors have found that a blood sample containing HbS shows a greater than 5% reduction in the second absorbance value measured at a wavelength selected from 422-440 nm, 422-432 nm, 425-435 nm, 425-430 nm, 425 nm, or 427 nm compared to the first absorption value measured at a wavelength selected from 400-421 nm, 410-420 nm, 408-418 nm, 410-415 nm, 412 nm, or 415 nm. The inventors expect HbC to show a similar absorption behavior as HbS.

TABLE 5A

The percent reduction in absorbance at 415 nm vs 425 nm and the presence or absence of HbS (blood sample mixed with 2.49M phosphate buffer comprising saponin for measurement at 415 nm and blood sample mixed with 2.49M phosphate buffer comprising saponin and sodium metabisulfite for measurement at 425 nm, and incubated at room temperature for about 5-30 minutes)

| Percent reduction | HbS |
|---|---|
| <5% | Absent |
| ≥5 | Present |

The inventors have found that the percent reduction of 5-30% in absorbance at 425 nm when a blood sample is mixed with 2.49M phosphate buffer, saponin, and sodium metabisulfite compared to absorbance at 415 nm when the blood sample is mixed with 2.49M phosphate buffer and saponin indicates that the blood sample is from a subject having SCT (i.e., heterozygous HbS with HbA/HbF) and when the percent reduction under the same conditions is greater than 30%, the blood sample is from a subject having SCD (homozygous HbSS). This is shown in Table 5B below:

TABLE 5B

The percent reduction in absorbance at 415 nm vs 425 nm and the identification of SCT/SCD (blood sample mixed with 2.49M phosphate buffer comprising saponin for measurement at 415 nm and blood sample mixed with 2.49M phosphate buffer comprising saponin and sodium metabisulfite for measurement at 425 nm, and incubated at room temperature for about 5-30 minutes)

| Percent reduction | Test Prediction |
|---|---|
| 5-30% | Sickle cell trait (Heterozygous HbS with HbA/HbF) |
| >30% | Sickle cell disease (Homozygous HbSS) |

The percent reduction method can be employed to identify the presence or absence of SCT or SCD in a subject based on the percent reduction values.

In some embodiments, an in vitro method of identifying the presence or absence of SCT or SCD in a subject comprises: a) measuring a first absorbance of a blood sample from the subject under an oxygenated condition at 400-421 nm; b) measuring a second absorbance of said blood sample under a deoxygenated condition at 422-440 nm; c) calculating a percent reduction in the second absorbance compared to the first absorbance; and d) identifying the presence or absence of SCT or SCD in the subject based on the percent reduction.

In some embodiments, an in vitro method of identifying the presence or absence of SCT or SCD in a subject comprises: (a) mixing a first part of a blood sample from the subject with a first physiologically acceptable buffer comprising a detergent to obtain a first sample-buffer mixture; (b) measuring a first absorbance of the first sample-buffer mixture at 400-421 nm; (c) mixing a second part of said blood sample with a second physiologically acceptable buffer comprising a detergent and a reducing agent to obtain a second sample-buffer mixture; (d) measuring a second absorbance of the second sample-buffer mixture at 422-440 nm; (e) calculating a percent reduction in the second absorbance compared to the first absorbance; and (f) identifying the presence or absence of SCT or SCD in the subject based on the percent reduction.

In some embodiments, the in vitro method of identifying the presence or absence of SCT or SCD in a subject comprises: (a) mixing a first part of a blood sample obtained from the subject with a 1.7-2.8 M phosphate buffer comprising saponin to obtain a first sample-buffer mixture; (b) measuring a first absorbance of the first sample-buffer mixture at a wavelength selected from 400-421 nm, 410-420 nm, 408-421 nm, 410-415 nm, 412 nm, or 415 nm; (c) mixing a second part of said blood sample with a 1.7-2.8 M phosphate buffer comprising saponin and sodium metabisulfite to obtain a second sample-buffer mixture; (d) measuring a second absorbance of the second sample-buffer mixture at a wavelength selected from 422-440 nm, 422-432 nm, 425-435 nm, 425-430 nm, 425 nm, or 427 nm; (e) calculating a percent reduction in the second absorbance compared to the first absorbance; and (f) identifying the presence or absence of SCT or SCD in the subject based on the percent reduction.

In some embodiments, the in vitro method of identifying the presence or absence of SCT or SCD in a subject comprises: (a) mixing a first part of a blood sample obtained from the subject with 2.49M phosphate buffer comprising saponin to obtain a first sample-buffer mixture; (b) measuring a first absorbance of the first sample-buffer mixture at a wavelength selected from 400-421 nm, 410-420 nm, 408-421 nm, 410-415 nm, 412 nm, or 415 nm; (c) mixing a second part of said blood sample with 2.49M phosphate buffer comprising saponin and sodium metabisulfite to obtain a second sample-buffer mixture; (d) measuring a second absorbance of the second sample-buffer mixture at a wavelength selected from 422-440 nm, 422-432 nm, 425-435 nm, 425-430 nm, 425 nm, or 427 nm; (e) calculating a percent reduction in the second absorbance compared to the first absorbance; and (f) identifying the presence or absence of SCT or SCD in the subject based on the percent reduction.

Although the present disclosure explicitly discloses threshold ratio values or threshold percent reduction values for certain phosphate buffer concentrations, the disclosure clearly contemplates a range of phosphate buffer concentrations and different types of buffers that could be employed to carry out the methods of the disclosure. Based on the teachings of the present disclosure, one of ordinary skill in the art could arrive at threshold ratio values or threshold percent reduction values for a different phosphate buffer concentration or for a different buffer type without undue experimentation. Accordingly, threshold ratio values or threshold percent reduction values for a range of phosphate buffer concentrations or for different types of buffers are encompassed by the present disclosure. Similarly, one of ordinary skill in the art could device ways other than those described herein to expose a blood sample to oxygenated and deoxygenated conditions and still arrive at the findings of the present disclosure. Such alternative ways to expose a blood sample to oxygenated and deoxygenated conditions to identify the presence or absence of HbS or HbC in a blood sample or the presence or absence of SCT or SCD in a subject are encompassed by the present disclosure. In other words, if the underlying premise of a method of identifying the presence or absence of HbS or HbC in a blood sample or the presence or absence of SCT or SCD in a subject is the decrease in absorbance exhibited by HbS or HbC under deoxygenated conditions, all such methods, systems, and kits thereof are encompassed by the present disclosure.

The Kinetics Method:

In some embodiments, the present disclosure provides an in vitro method of identifying the presence or absence of SCT or SCD in a subject, said method comprising: (a)

measuring a change in absorption of a blood sample under a deoxygenated condition across 380 nm to 600 nm over a time period of about 0 minute to 30 minutes; (b) determining the rate of change of absorption; and (c) identifying the presence or absence of SCT or SCD in the subject based on the rate of change of absorption.

In this embodiment, the absorbance of a blood sample collected from a subject is measured under deoxygenated conditions across 380 nm to 600 nm from about 0 minute (after exposing the blood sample to deoxygenated conditions) to about 30 minutes or from about 1 minute (after exposing the blood sample to deoxygenated conditions) to 30 minutes. The rate of change of absorption is determined and based on this rate, the presence or absence of SCT or SCD in the subject is identified. The inventors have found that a blood sample from a SCD subject shows a greater rate of change in absorption compared to the rate of change in absorption shown by a blood sample from a SCT subject. A blood sample from a normal/healthy subject shows a very minor change in absorption, if any, across 380 nm to 600 nm from time zero to about 30 minutes.

The absorbance of the blood sample under deoxygenated condition is measured across the spectrum, such as from 380 nm to 580 nm, 380 nm to 560 nm, 380 nm to 550 nm, 380 nm to 520 nm, 380 nm to 500 nm, from 380 nm to 480 nm, from 380 nm to 450 nm, or from 380 nm to 440 nm.

The change in absorption across the spectrum is measured over a period time such as from about 0 minute to about 30 minutes or from about 1 minute to about 30 minutes. The inventors have observed that the rate of change in absorbance remains more or less the same from about 0 minute or 1 minute after exposure to deoxygenated conditions up to about 380 seconds. In some embodiments, the change in absorbance of the blood sample is measured over a period of time from about 0 minute to about 30 minutes, from about 1 minute to about 30 minutes, from about 1 minute to about 20 minutes, from about 1 minute to about 15 minutes, from about 1 minute to about 10 minutes, from about 1 minute to about 6 minutes, or from about 1 minute to about 5 minutes.

In some embodiments, the rate of change in absorbance is expressed as change in absorbance per minute or change in absorbance per second.

In some embodiments, the deoxygenated condition comprises mixing the subject's blood sample with a physiologically acceptable buffer comprising a detergent and a reducing agent to provide a sample-buffer mixture. The physiologically acceptable buffer, the detergent, the reducing agent, and their respective concentrations are as described herein.

Accordingly, in some embodiments, the in vitro method of identifying the presence or absence of SCT or SCD in a subject, comprises: (a) mixing a blood sample obtained from the subject with a physiologically acceptable buffer comprising a detergent and a reducing agent to obtain a sample-buffer mixture; (b) measuring an absorbance of the sample-buffer mixture from 380 nm to 600 nm, from 380 nm to 550 nm, from 380 nm to 520 nm, or from 380 nm to 480 nm, for a time period selected from about 0 minute to about 30 minutes, about 1 minute to about 30 minutes, about 1 minute to about 20 minutes, from about 1 minute to about 15 minutes, from about 1 minute to about 10 minutes, from about 1 minute to about 6 minutes, or from about 1 minute to about 5 minutes; (c) calculating the rate of change of absorbance; and (d) identifying the presence or absence of SCD or SCT in the subject based on the rate of change of absorbance.

In some embodiments, the in vitro method of identifying the presence or absence of SCT or SCD in a subject, comprises: (a) mixing a blood sample obtained from the subject with a 1.7 M-2.8M phosphate buffer comprising a detergent and a reducing agent to obtain a sample-buffer mixture; (b) measuring an absorbance of the sample-buffer mixture from 380 nm to 600 nm, from 380 nm to 550 nm, from 380 nm to 520 nm, or from 380 nm to 480 nm, for a time period selected from about 0 minute to about 30 minutes, about 1 minute to about 30 minutes, from about 1 minute to about 20 minutes, from about 1 minute to about 15 minutes, from about 1 minute to about 10 minutes, from about 1 minute to about 6 minutes, or from about 1 minute to about 5 minutes; (c) calculating the rate of change of absorbance; and (d) identifying the presence or absence of SCD or SCT in the subject based on the rate of change of absorbance.

In an exemplary embodiment, when a blood sample is mixed with 2.49 M phosphate buffer comprising 0.4% saponin and 2% sodium metabisulphite and the rate of change in absorbance of this sample-buffer mixture is measured from about 0 minute to about 380 seconds, the rate of change in absorbance of about 0.067/min indicates that the sample is from a SCD subject whereas the rate of change in absorbance of about 0.052/min indicates that the sample is from a SCT subject.

Relative Concentration of HbS or HbC

The present disclosure also provides an in vitro method for identifying the relative percentage of HbS or HbC in a blood sample. In some embodiments, said method comprises: a) measuring a first absorbance of said blood sample under oxygenated conditions; b) measuring a second absorbance of said blood sample under deoxygenated conditions; c) calculating 30% of the first absorbance to provide a value ("N"); d) subtracting N from the first absorbance and the second absorbance to provide modified first absorbance and modified second absorbance, respectively; and e) determining the relative percentage of HbS or HbC in the blood sample from said modified first absorbance and modified second absorbance.

To determine relative percentage of HbS or HbC in the blood sample, a value (referred to as "N") that is 30% of the first absorbance is calculated. The 30% of the first absorbance is calculated as about 30% of the absorption at this wavelength is due to interfering substances other than haemoglobin (Hb). The value N is subtracted from the first absorbance and the second absorbance to provide modified first absorbance and modified second absorbance, respectively. The modified first absorbance is representative of total Hb (HbA+HbF+HbS+HbC and other variants of Hb, if present) in the blood sample whereas modified second absorbance is representative of Hb other than HbS or HbC (i.e. all Hb variants other than HbS or HbC). From modified first absorbance and modified second absorbance, a percentage of Hb other than HbS or HbC is calculated ((modified second absorbance/modified first absorbance)×100). Subtracting this percentage from 100 provides a percentage of HbS or HbC in the blood sample.

In some embodiments, the oxygenated conditions comprise mixing the subject's blood sample with a physiologically acceptable buffer comprising a detergent, but not a reducing agent, to provide a first sample-buffer mixture. The physiologically acceptable buffer, the detergent, and their respective concentrations are as described herein.

In some embodiments, the deoxygenated conditions comprise mixing the subject's blood sample with a physiologically acceptable buffer comprising a detergent and a reducing agent to provide a second sample-buffer mixture. The physiologically acceptable buffer, the detergent, the reducing agent, and their respective concentrations are as described herein.

The absorbance of the first sample-buffer mixture (first absorbance) is measured at a wavelength selected from 400-421 nm, 410-420 nm, 408-418 nm, 410-415 nm, 412 nm, or 415 nm and the absorbance of the second sample-buffer mixture (second absorbance) is measured at a wavelength selected from 422-440 nm, 422-432 nm, 425-440 nm, 425-430 nm, 425 nm, or 427 nm.

Accordingly, in some embodiments, the in vitro method of identifying the relative percentage of HbS or HbC in a blood sample comprises: (a) mixing a first part of said blood sample with a first physiologically acceptable buffer comprising a detergent to obtain a first sample-buffer mixture; (b) measuring a first absorbance of the first sample-buffer mixture at 400-421 nm, 410-420 nm, 408-418 nm, 410-415 nm, 412 nm, or 415 nm; (c) mixing a second part of said blood sample with a second physiologically acceptable buffer comprising a detergent and a reducing agent to obtain a second sample-buffer mixture; (d) measuring a second absorbance of the second sample-buffer mixture at 422-440 nm, 422-432 nm, 425-440 nm, 425-430 nm, 425 nm, or 427 nm; (e) calculating 30% of the first absorbance to provide a value ("N"); (f) subtracting N from the first absorbance and the second absorbance to provide modified first absorbance and modified second absorbance, respectively; and (g) determining the relative percentage of HbS or HbC in the blood sample from said modified first absorbance and modified second absorbance.

In some embodiments, the first and the second sample-buffer mixtures are incubated at room temperature for about 5 minutes to about 30 minutes prior to measuring their absorption. In some embodiments, the sample-buffer mixture is incubated at room temperature for about 5 minutes to about 25 minutes, about 5 minutes to about 20 minutes, about 5 minutes to about 15 minutes, or about 5 minutes to about 10 minutes. In some embodiments, the sample-buffer mixture is incubated at room temperature for about 5, 6, 7, 8, 9, 10, 11, 12, 13, 14, 15, 20, 21, 22, 23, 24, 25, 26, 27, 28, 29, or 30 minutes.

The relative concentration of HbS or HbC is useful in determining the clinical severity of sickle cell condition in a subject. For example, a subject may have SCD; however, the subject may produce sufficient HbF (fetal Hb) in his/her blood. A blood sample from such a subject will have relatively lower percentage of HbS although he/she has SCD as the blood has more HbF. In view of this relatively low concentration of HbS in the subject's blood, a clinician may decide that the subject does not need any intervention or may need only occasional intervention to manage SCD. On the other hand, a subject may have SCT; however, the relative concentration of HbS in the subject's blood could be high (as the subject may produce lower amounts of HbA due to genetic abnormality in HbA production and HbF) prompting a clinician to prescribe an intervention to manage SCT. Thus, the relative concentration of HbS or HbC in a blood sample helps in determining the clinical condition of the subject and manage the sickle cell condition accordingly.

The methods of the present disclosure provide a simple yet very accurate way of identifying the presence or absence of HbS or HbC in a blood sample and the presence or absence of SCT or SCD in a subject. The present methods employ simple reagents and are thus inexpensive. Further, the methods are easy to perform in a point-of-care setting and can be carried out using a simple device. For example, the methods described herein can be carried our using a simple point-of-care device based on the present disclosure without the need for bulky, expensive equipments required for current confirmatory tests. The methods of the present disclosure also obviate the need to transport blood to centralized laboratories. The present methods also work with low quantities of blood (e.g., finger prick) and there is no need to have trained personnel to perform the methods and/or operate the device.

Kits

The present disclosure also provides kits for performing the in vitro methods of the present disclosure. In some embodiments, the kit comprises a physiologically acceptable buffer, a detergent, a reducing agent, and a document comprising instructions to carry out the method and a table providing threshold ratio values or threshold percent reduction values to identify the presence or absence of HbS or HbC, to determine the relative concentration of HbS or HBC, or to identify the presence or absence of SCT or SCD. In some embodiments, the physiologically acceptable buffer, the detergent, the reducing agent, and their respective concentrations are as described herein. In some embodiments, threshold ratio values or threshold percent reduction values are as described herein. The detergent and the reducing agent are added to the buffer solution immediately prior (e.g., about 5 minutes up to 4 hours prior) to mixing with a blood sample.

As discussed above, although the present disclosure explicitly discloses threshold ratio values or threshold percent reduction values for certain phosphate buffer concentrations, the disclosure clearly contemplates a range of phosphate buffer concentrations and different types of buffers (e.g., carbonate, citrate, acetate, HEPS, MOPS, etc.) that could be employed to carry out the methods of the disclosure. Based on the teachings of the present disclosure, one of ordinary skill in the art could arrive at threshold ratio values or threshold percent reduction values for a different phosphate buffer concentration or for a different buffer type without undue experimentation. Accordingly, threshold ratio values or threshold percent reduction values for a range of phosphate buffer concentrations or for different types of buffers are encompassed by the present disclosure and are expected to be included in the table in the document present in the kit.

In some embodiments, a buffer in the kit is provided as a ready-to-use (RTU) solution of desired concentration. The RTU solution of the buffer is stable at room temperature as well as 4° C.

In some embodiments, a concentrated stock solution of a buffer is provided. In some embodiments, a 2×, 4×, 5×, or 10× concentrated stock solution of a buffer is provided in the kit. To dilute this stock solution to a working solution, the kit may include sterile distilled water.

In some other embodiments, the kit comprises buffer components (e.g., monobasic and dibasic phosphate salts) in solid form. Preferably, pre-determined amounts of these buffer components will be provided and instructions as to how to prepare a buffer solution using these pre-determined amounts will be provided. To prepare a buffer solution from solid components, the kit may include sterile distilled water.

The detergent in the kit can be provided in a solid form or a solution form.

In some embodiments, the detergent in the kit is provided as a ready-to-use (RTU) solution of desired concentration. The RTU solution of the detergent is preferably stored at 4° C.

In some embodiments, a concentrated stock solution of a detergent is provided in the kit. In some embodiments, a 10×-50× concentrated stock solution of a detergent is provided in the kit. For example, in some embodiments, a 10×, 12.5×, 15×, 20×, 25×, 30×, 40×, or 50× concentrated stock solution of a detergent is provided in the kit. To dilute this stock solution to a working solution, the kit may include sterile distilled water.

In some other embodiments, the kit comprises a detergent in a solid form. Preferably, a pre-determined amount of the detergent will be provided and instructions as to how to prepare a detergent solution using the pre-determined amount will be provided. To prepare a solution of detergent from solid detergent, the kit may include sterile distilled water.

Preferably, the reducing agent such as sodium metabisulfite is supplied in a solid form as a solution of the reducing agent may not be very stable. Therefore, in some embodiments, the kit comprises the reducing agent in solid form.

In an exemplary embodiment, a kit comprises a vial containing a solution of phosphate buffer, a vial containing saponin as a detergent, a vial containing sodium metabisulfite as a reducing agent, and a document comprising instructions to carry out the method and a table providing threshold ratio values or threshold percent reduction values for the phosphate buffer included in the kit to identify the presence or absence of HbS or HbC or to identify the presence or absence of SCT or SCD. In this embodiment, saponin and sodium metabisulfite are added to the buffer solution immediately prior (e.g., about 5 minutes up to 4 hours prior) to mixing with a blood sample.

In the ratio method, both the first and the second absorbance are measured under deoxygenated conditions. Therefore, only one buffer comprising the detergent and the reducing agent is needed to perform the ratio method. In the percent reduction method, the first absorbance is measured under oxygenated conditions and the second absorbance is measured under deoxygenated conditions. Therefore, two buffers are needs to perform the ratio method—a first buffer comprising the detergent but not the reducing agent (oxygenated conditions) and a second buffer comprising the detergent and the reducing agent (deoxygenated conditions). Since the kit provides the detergent and the reducing agent separately, one of ordinary skill in the art can use the same kit to prepare both the buffers—one comprising the detergent but not the reducing agent and the other comprising both the detergent and the reducing agent. Depending on which method to use, one of ordinary skill in the art can decide which buffers to prepare using the kit.

In another exemplary embodiment, a kit comprises a vial containing a solution of 2.365M phosphate buffer, a vial containing saponin, a vial containing sodium metabisulfite, and a document comprising instructions to carry out the method and a table providing threshold ratio values or threshold percent reduction values for the phosphate buffer included in the kit to identify the presence or absence of HbS or HbC or to identify the presence or absence of SCT or SCD. In this embodiment, saponin and sodium metabisulfite are added to the buffer solution immediately prior (e.g., about 5 minutes up to 4 hours prior) to mixing with a blood sample.

In another exemplary embodiment, a kit comprises a vial containing a solution of 2.083M phosphate buffer, a vial containing saponin, a vial containing sodium metabisulfite, and a document comprising instructions to carry out the method and a table providing threshold ratio values or threshold percent reduction values for the phosphate buffer included in the kit to identify the presence or absence of HbS or HbC or to identify the presence or absence of SCT or SCD. In this embodiment, saponin and sodium metabisulfite are added to the buffer solution immediately prior (e.g., about 5 minutes up to 4 hours prior) to mixing with a blood sample.

In yet another exemplary embodiment, a kit comprises a monobasic salt of sodium phosphate or potassium phosphate, a dibasic salt of sodium phosphate or potassium phosphate, saponin, sodium metabisulfite, and a document comprising instructions to prepare a buffer solution using the monobasic and dibasic phosphate salts, instructions to carry out the method and a table providing threshold ratio values or threshold percent reduction values for the phosphate buffer that would be prepared using the kit to identify the presence or absence of HbS or HbC or to identify the presence or absence of SCT or SCD. In this embodiment, the buffer solution can be prepared by a user and stored at room temperature or at 4° C. Saponin and sodium metabisulfite are added to the buffer solution immediately prior (e.g., about 5 minutes up to 4 hours prior) to mixing with a blood sample.

In some embodiments, the kit also comprises blood collection containers comprising an anti-coagulant. In some embodiments, the kit comprises lancets to perform finger pricking.

Devices

The present disclosure provides a device for performing the in vitro methods of identifying the presence or absence of HbS or HbC in a blood sample, identifying the relative percentage of HbS or HbC in a blood sample, and identifying the presence or absence of SCT or SCD in a subject.

In an exemplary embodiment, the device comprises (a) a light source for emitting light in the wavelength of 380-600 nm; (b) a detector for detecting the first absorbance and the second absorbance; and (c) a processor comprising instructions to calculate the ratio of the second absorbance to the first absorbance or a ratio of the first absorbance to the second absorbance as described in the ratio method or instructions to calculate the percent reduction in the second absorbance compared to the first absorbance as described in the percent reduction method.

In another exemplary embodiment, the device comprises (a) a light source for emitting light in the wavelength of 380-600 nm; (b) a detector for detecting the first absorbance and the second absorbance; (c) a monochromator; and (d) a processor comprising instructions to calculate the ratio of the second absorbance to the first absorbance or a ratio of the first absorbance to the second absorbance as described in the ratio method or instructions to calculate the percent reduction in the second absorbance compared to the first absorbance as described in the percent reduction method. In some embodiments, the monochromator is comprises an entrance slit (to narrow the light beam to a usable size), a dispersion device (usually a diffraction grating or prism that separates polychromatic white light into bands of monochromatic light of a single wavelength), and an exit slit (to select the desired monochromatic wavelength). In some embodiments, the monochromator is positioned between the light source and the detector.

Figure 5:
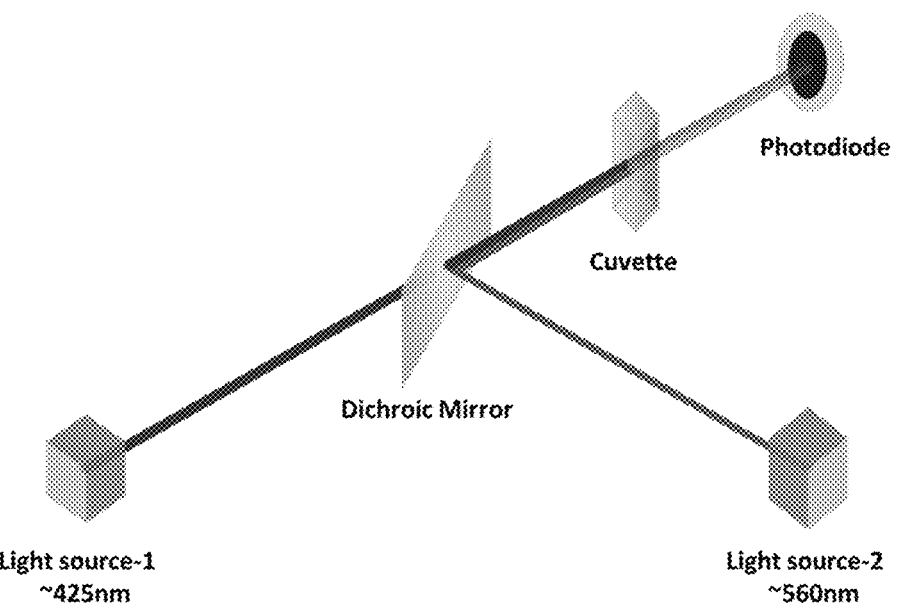
FIG. 5 shows a schematic of the components of an exemplary device according to the present disclosure.

In some embodiments, the device is a single beam or double beam dispersive-type spectrophotometer known in the art that is modified to comprise a processor comprising instructions to calculate the ratio of the second absorbance to the first absorbance or a ratio of the first absorbance to the second absorbance as described in the ratio method or instructions to calculate the percent reduction in the second absorbance compared to the first absorbance as described in the percent reduction method. FIG. 5 shows a schematic of the components of an exemplary device according to the present disclosure.

Methods for Managing/Treating Sickle Cell Conditions

In some embodiments, provided herein are methods for treating or managing sickle cell conditions.

In some embodiments, a method for treating/managing SCD in a subject comprises: (a) measuring a first absorbance of a blood sample from the subject under a deoxygenated condition at 420-440 nm; (b) measuring a second absorbance of said blood sample under the deoxygenated condition at 545-565 nm; (c) calculating a ratio of the second absorbance to the first absorbance or a ratio of the first absorbance to the second absorbance; (d) identifying the presence or absence of SCD in the subject based on the ratio; and (e) if the subject has SCD, managing the SCD by administering an appropriate treatment or therapy to the subject. In some embodiments, the deoxygenated conditions are as described herein.

In some embodiments, a method for treating/managing SCD in a subject comprises: (a) measuring a first absorbance of a blood sample from the subject under an oxygenated condition at 400-421 nm; (b) measuring a second absorbance of said blood sample under a deoxygenated condition at 422-440 nm; (c) calculating a percent reduction in the second absorbance compared to the first absorbance; (d) identifying the presence or absence of SCD in the subject based on the percent reduction and (e) if the subject has SCD, managing the SCD by administering an appropriate treatment or therapy to the subject. In some embodiments, the oxygenated and deoxygenated conditions are as described herein.

In some embodiments, a method for treating/managing SCD in a subject comprises: (a) mixing a blood sample from the subject with a physiologically acceptable buffer comprising a detergent and a reducing agent to obtain a sample-buffer mixture; (b) measuring a first absorbance of the sample-buffer mixture at 420-440 nm; (c) measuring a second absorbance of the sample buffer mixture at 545-565 nm; (d) calculating a ratio of the second absorbance to the first absorbance or a ratio of the first absorbance to the second absorbance; (e) identifying the presence or absence of SCD in the subject based on the ratio; and (f) if the subject has SCD, managing the SCD by administering an appropriate treatment or therapy to the subject. In some embodiments, the physiologically acceptable buffer, the detergent, and the reducing agents are as described herein.

In some embodiments, a method for treating/managing SCD in a subject comprises: (a) mixing a first part of a blood sample from the subject with a first physiologically acceptable buffer comprising a detergent to obtain a first sample-buffer mixture; (b) measuring a first absorbance of the first sample-buffer mixture at 400-421 nm; (c) mixing a second part of said blood sample with a second physiologically acceptable buffer comprising a detergent and a reducing agent to obtain a second sample-buffer mixture; (d) measuring a second absorbance of the second sample-buffer mixture at 422-440 nm; (e) calculating a percent reduction in the second absorbance compared to the first absorbance; (f) identifying the presence or absence of SCD in the subject based on the percent reduction; and (g) if the subject has SCD, managing the SCD by administering an appropriate treatment or therapy to the subject. In some embodiments, the physiologically acceptable buffer, the detergent, and the reducing agents are as described herein.

In some embodiments, a method for treating/managing a sickle cell condition in a subject comprises: a) measuring a first absorbance of a blood sample obtained from the subject under oxygenated conditions; b) measuring a second absorbance of said blood sample under deoxygenated conditions; c) calculating 30% of the first absorbance to provide a value ("N"); d) subtracting N from the first absorbance and the second absorbance to provide modified first absorbance and modified second absorbance, respectively; e) determining the relative percentage of HbS or HbC in said blood sample from said modified first absorbance and modified second absorbance; and f) managing the sickle cell condition in the subject based on the relative percentage of HbS or HbC.

In some embodiments, a method for treating/managing a sickle cell condition in a subject comprises: (a) mixing a first part of a blood sample from the subject with a first physiologically acceptable buffer comprising a detergent to obtain a first sample-buffer mixture; (b) measuring a first absorbance of the first sample-buffer mixture at 400-421 nm, 410-420 nm, 408-418 nm, 410-415 nm, 412 nm, or 415 nm; (c) mixing a second part of said blood sample with a second physiologically acceptable buffer comprising a detergent and a reducing agent to obtain a second sample-buffer mixture; (d) measuring a second absorbance of the second sample-buffer mixture at 422-440 nm, 422-432 nm, 425-440 nm, 425-430 nm, 425 nm, or 427 nm; (e) calculating 30% of the first absorbance to provide a value ("N"); (f) subtracting N from the first absorbance and the second absorbance to provide modified first absorbance and modified second absorbance, respectively; (g) determining the relative percentage of HbS or HbC in the blood sample from said modified first absorbance and modified second absorbance; and (h) managing the sickle cell condition in the subject based on the relative percentage of HbS or HbC.

Exemplary treatments or therapies to manage sickle cell conditions include administration of hydroxyurea, L-glutamine powder, crizanlizumab, voxelotor, and/or folic acid supplements. If the subject is identified as having a sickle cell condition based on the in vitro methods of the present disclosure, a physician can manage the condition in the subject by prescribing one or more of these treatments/therapies.

It is to be understood that the foregoing descriptive matter is illustrative of the disclosure and not a limitation. While considerable emphasis has been placed herein on the particular features of this disclosure, it will be appreciated that various modifications can be made, and that many changes can be made in the preferred embodiments without departing from the principles of the disclosure. Those skilled in the art will recognize that the embodiments herein can be practiced with modification within the spirit and scope of the embodiments as described herein. Similarly, additional embodiments and features of the present disclosure will be apparent to one of ordinary skill in art based upon description provided herein.

Descriptions of well-known/conventional methods/steps and techniques are omitted so as to not unnecessarily obscure the embodiments herein. Further, the disclosure herein provides for examples illustrating the above-described embodiments, and in order to illustrate the embodiments of the present disclosure certain aspects have been employed. The examples used herein for such illustration are intended merely to facilitate an understanding of ways in which the embodiments herein may be practiced and to further enable those of skill in the art to practice the embodiments herein. Accordingly, the following examples should not be construed as limiting the scope of the embodiments herein.

EXAMPLES

Example 1: Determination of Threshold Values Using the Ratio Method (Known Samples)

In this study, known samples were used to analyze the absorption at 427 nm and 555 nm under deoxygenated conditions using 2.365M phosphate buffer.

Sample Collection: Venous blood samples were collected in $K_2$EDTA coated collection tubes and stored at 2° C.-8° C. until the tests were carried out.

Buffer Preparation: Phosphate buffer of 2.365M concentration was prepared by adding monobasic salt 1.178 M (160.3 g/L) and dibasic salt 1.187 M (206.8 g/L). Saponin and sodium metabisulfite at 2% final concentration were added to the buffer. The freshly prepared buffer was used for testing within 4 hours of preparation.

Testing: 5 μL of blood sample was added to the tube containing 1 mL of buffer, mixed well and incubated at room temperature for 15 minutes. The sample-buffer mixture loaded into a glass cuvette of 2 mm pathlength and measured the optical absorption spectrum using a spectrophotometer (Denovix DS-11 FX+, USA) at 427 nm (first absorbance) and at 555 nm (second absorbance).

Analysis: The analysis of the samples involved calculating the threshold value (α), by taking the ratios of second absorbance to first absorbance (A555/A427) or first absorbance to second absorbance (A427/A555). The range of threshold value (α) indicates the presence or absence of HbS and the presence or absence of SCT/SCD.

Analysis of Threshold Value (α):

TABLE 6

| | | | | | Disease condition |
|---|---|---|---|---|---|
| Sample ID | A555 | A427 | Threshold Value (α) (A555/A427) | Threshold Value (α) (A427/A555) | (Previously known) |
| Sample -1 | 0.232 | 1.745 | 0.133 | 7.522 | Normal |
| Sample-2 | 0.216 | 1.646 | 0.131 | 7.620 | Normal |
| Sample-3 | 0.151 | 0.769 | 0.196 | 5.093 | SCT |
| Sample-4 | 0.203 | 1.132 | 0.179 | 5.576 | SCT |
| Sample-5 | 0.182 | 1.030 | 0.177 | 5.659 | SCT |
| Sample-6 | 0.156 | 0.762 | 0.205 | 4.885 | SCT |
| Sample -7 | 0.156 | 0.869 | 0.180 | 5.571 | SCT |
| Sample-8 | 0.180 | 0.824 | 0.218 | 4.578 | SCT |
| Sample-9 | 0.193 | 1.034 | 0.187 | 5.358 | SCT |
| Sample-10 | 0.178 | 0.986 | 0.181 | 5.539 | SCT |
| Sample-11 | 0.187 | 1.033 | 0.181 | 5.524 | SCT |
| Sample-12 | 0.163 | 0.755 | 0.216 | 4.632 | SCT |
| Sample-13 | 0.170 | 0.651 | 0.261 | 3.829 | SCD |
| Sample-14 | 0.138 | 0.448 | 0.308 | 3.246 | SCD |
| Sample-15 | 0.125 | 0.407 | 0.307 | 3.256 | SCD |

Based on these test results, the a value range for different sickle conditions for the above-mentioned buffer condition was arrived at as given below:

TABLE 7

| Threshold Value (α) ($A_{555}/A_{427}$) | Threshold Value (α) ($A_{427}/A_{555}$) | HbS | SCT/SCD |
|---|---|---|---|
| <0.16 | >6 | Absent | Control/Healthy (Negative) |

TABLE 7-continued

| Threshold Value (α) ($A_{555}/A_{427}$) | Threshold Value (α) ($A_{427}/A_{555}$) | HbS | SCT/SCD |
|---|---|---|---|
| 0.16-0.24 | 4-6 | Present | Sickle cell trait (Heterozygous HbS with HbA/HbF) |
| >0.24 | <4 | Present | Sickle cell disease (Homozygous HbSS) |

Example 2: Determination of Threshold Values Using the Ratio Method (Known Samples)

In this study, known samples were used to analyze the absorption at 427 nm and 555 nm under deoxygenated conditions using 2.083M phosphate buffer.

Sample Collection: Venous blood samples were collected in $K_2$EDTA coated collection tubes and stored at 2° C.-8° C. until the tests were carried out.

Buffer Preparation: Phosphate buffer of 2.083 M concentration was prepared by adding Monobasic salt 1.178 M (160.3 g/L) and dibasic salt 0.905 M (156.2 g/L). Saponin and sodium metabisulfite at 2% final concentration were added to the buffer. The freshly prepared buffer was used for testing within 4 hours of preparation.

Testing: 5 μL of blood sample was added to the tube containing 1 mL of buffer, mixed well and incubated at room temperature for 15 minutes. The sample-buffer mixture loaded into a glass cuvette of 2 mm pathlength and measured the optical absorption spectrum using a spectrophotometer (Denovix DS-11 FX+, USA) at 427 nm (first absorbance) and at 555 nm (second absorbance).

Analysis: The analysis of the samples involves calculating the threshold value (α), by taking the ratios of second absorbance to first absorbance (A555/A427) or first absorbance to second absorbance (A427/A555). The range of threshold value (α) indicates the presence or absence of HbS and the presence or absence of SCT/SCD.

TABLE 8

| | | | | | Disease condition |
|---|---|---|---|---|---|
| Sample ID | A555 | A427 | Threshold Value (α) (A555/A427) | Threshold Value (α) (A427/A555) | (Previously known) |
| Sample -1 | 0.122 | 0.911 | 0.134 | 7.451 | SCT |
| Sample-2 | 0.150 | 1.079 | 0.139 | 7.184 | SCT |
| Sample-3 | 0.107 | 0.823 | 0.131 | 7.627 | SCT |
| Sample-4 | 0.133 | 1.043 | 0.128 | 7.808 | SCT |
| Sample-5 | 0.125 | 0.911 | 0.137 | 7.270 | SCT |
| Sample-6 | 0.2 | 1.503 | 0.134 | 7.489 | SCT |
| Sample -7 | 0.118 | 0.712 | 0.166 | 6.036 | SCD |
| Sample-8 | 0.103 | 0.543 | 0.190 | 5.259 | SCD |
| Sample-9 | 0.137 | 0.845 | 0.163 | 6.131 | SCD |

Based on these test results, the a value range for different sickle conditions for the above-mentioned buffer condition was arrived at as given below:

TABLE 9

| Threshold Value ($\alpha$) ($A_{555}/A_{427}$) | Threshold Value ($\alpha$) ($A_{555}/A_{427}$) | HbS | SCT/SCD |
|---|---|---|---|
| <0.11 | >8 | Absent | Control/Healthy (Negative) |
| 0.11-0.15 | 6.5-8 | Present | Sickle cell trait (Heterozygous HbS with HbA/HbF) |
| >0.15 | <6.5 | Present | Sickle cell disease (Homozygous HbSS) |

Example 3: Analysis of Blood Samples Using the Ratio Method (Blind Study)

In this study, unknown samples were analyzed using 2.365M phosphate buffer to identify the presence or absence of HbS and the presence or absence of SCD or SCT.

Sample Collection: Venous blood samples were collected in K$_2$EDTA coated collection tubes and stored at 2° C.-8° C. until the tests were carried out.

Buffer Preparation: Phosphate buffer of 2.365M concentration was prepared by adding monobasic salt 1.178 M (160.3 g/L) and dibasic salt 1.187 M (206.8 g/L). Saponin and sodium metabisulfite at 2% final concentration were added to the buffer. The freshly prepared buffer was used for testing within 4 hours of preparation.

Testing: 5 µL of blood sample was added to the tube containing 1 mL of buffer, mixed well and incubated at room temperature for 15 minutes. The sample-buffer mixture loaded into a glass cuvette of 2 mm pathlength and measured the optical absorption spectrum using a spectrophotometer (Denovix DS-11 FX+, USA) at 427 nm (first absorbance) and at 555 nm (second absorbance).

Analysis: The analysis of the samples involved calculating the threshold value ($\alpha$), by taking the ratios of second absorbance to first absorbance (A555/A427) or first absorbance to second absorbance (A427/A555). Based on the threshold value ($\alpha$), the presence or absence of HbS and the presence or absence of SCT/SCD was identified using the ratio ranges obtained in Example 1.

TABLE 10

| | | Analysis of Threshold Value ($\alpha$) | | |
|---|---|---|---|---|
| Sample ID | A555 | A427 | Threshold Value ($\alpha$) (A555/A427) | Threshold Value ($\alpha$) (A427/A555) | Predicted Disease condition |
| Sample -1 | 0.085 | 0.452 | 0.19 | 5.318 | SCT |
| Sample-2 | 0.093 | 0.298 | 0.31 | 3.176 | SCD |
| Sample-3 | 0.109 | 0.611 | 0.178 | 5.606 | SCT |
| Sample-4 | 0.126 | 0.71 | 0.177 | 5.635 | SCT |
| Sample-5 | 0.141 | 0.708 | 0.199 | 5.018 | SCT |
| Sample-6 | 0.113 | 0.564 | 0.2 | 4.995 | SCT |

All the samples were cross-validated with gold-standard HPLC (high performance liquid chromatography) method which is currently used in the clinics to identify the zygosity or determine the Hb variants in the sample.

Example 4: Analysis of Blood Samples Using the Ratio Method (Blind Study)

In this study, unknown samples were analyzed using 2.083M phosphate buffer to identify the presence or absence of HbS and the presence or absence of SCD or SCT.

Sample Collection: Venous blood samples were collected in K$_2$EDTA coated collection tubes and stored at 2° C.-8° C. until the tests were carried out.

Buffer Preparation: Phosphate buffer of 2.083 M concentration was prepared by adding Monobasic salt 1.178 M (160.3 g/L) and dibasic salt 0.905 M (156.2 g/L). Saponin and sodium metabisulfite at 2% final concentration were added to the buffer. The freshly prepared buffer was used for testing within 4 hours of preparation.

Testing: 5 µL of blood sample was added to the tube containing 1 mL of buffer, mixed well and incubated at room temperature for 15 minutes. The sample-buffer mixture loaded into a glass cuvette of 2 mm pathlength and measured the optical absorption spectrum using a spectrophotometer (Denovix DS-11 FX+, USA) at 427 nm (first absorbance) and at 555 nm (second absorbance).

Analysis: The analysis of the samples involves calculating the threshold value ($\alpha$), by taking the ratios of second absorbance to first absorbance (A555/A427) or first absorbance to second absorbance (A427/A555). Based on the threshold value ($\alpha$), the presence or absence of HbS and the presence or absence of SCT/SCD was identified using the ratio ranges obtained in Example 2.

TABLE 11

| | | Analysis of Threshold Value ($\alpha$) | | |
|---|---|---|---|---|
| Sample ID | A555 | A427 | Threshold Value ($\alpha$) (A555/A427) | Threshold Value ($\alpha$) (A427/A555) | Predicted Disease condition |
| Sample -1 | 0.128 | 0.894 | 0.143 | 6.984 | SCT |
| Sample-2 | 0.118 | 0.712 | 0.165 | 6.034 | SCD |
| Sample-3 | 0.137 | 0.904 | 0.151 | 6.6 | SCT |
| Sample-4 | 0.142 | 0.992 | 0.143 | 6.986 | SCT |
| Sample-5 | 0.2 | 1.503 | 0.133 | 7.515 | SCT |
| Sample-6 | 0.126 | 0.911 | 0.138 | 7.236 | SCT |

All the samples were cross-validated with gold-standard HPLC (high performance liquid chromatography) method which is currently used in the clinics to identify the zygosity or determine the Hb variants in the sample.

Example 5: Analysis of Blood Samples Using the Percent Reduction Method

Sample Collection: Venous blood samples were collected in K$_2$EDTA coated collection tubes and stored at 2° C.-8° C. until the tests were carried out.

Buffer preparation (Deoxy): Phosphate buffer of 2.49 M concentration was prepared by adding monobasic salt 1.24 M (169 g/L) and dibasic salt 1.25 M (217 g/L). Saponin at 0.4% and sodium metabisulfite at 2% final concentration were added to the buffer. The freshly prepared buffer was used for testing within 4 hours of preparation.

Buffer preparation (Oxy): Phosphate buffer of 2.49 M concentration was prepared by adding monobasic salt 1.24 M (169 g/L) and dibasic salt 1.25 M (217 g/L). Saponin at 0.4% final concentration was added to the buffer.

Testing: 5 µL of blood sample was added to the tube containing 1 mL of buffer (Oxy and Deoxy), mixed well and incubated at room temperature for 15 minutes. The sample-buffer mixture loaded into a glass cuvette of 2 mm pathlength and measured the optical absorption spectrum using a spectrophotometer (Denovix DS-11 FX+, USA) at 427 nm (first absorbance) and at 555 nm (second absorbance).

Analysis: The analysis of the samples involved calculating the percentage reduction of absorbance between the peaks at 415 nm in Oxy buffer and 425 nm in Deoxy buffer. The range of percentage indicates the presence or absence of HbS and the presence or absence of SCT/SCD.

TABLE 12

| | | | Reduced absorbance from $A_{415}$ | |
|---|---|---|---|---|
| Sample ID | Wavelength | Absorbance | to $A_{425}$ in % | Condition |
| Control-Deoxy | 425 | 1.441 | | |
| Control | 415 | 1.4437 | 0.18701946 | Normal |
| Sample-19 Deoxy | 425 | 0.6662 | | |
| Sample-19 | 415 | 1.065 | 37.4460094 | SCD |
| Sample-9 Deoxy | 425 | 1.0648 | | |
| Sample-9 | 415 | 1.2211 | 12.7999345 | SCT |
| Sample-83 Deoxy | 425 | 0.6184 | | |
| Sample -83 | 415 | 0.725 | 14.7034483 | SCT |
| Sample-35 Deoxy | 425 | 1.0288 | | |
| Sample-35 | 415 | 1.4315 | 28.1313308 | SCT |
| Sample 47-Deoxy | 425 | 1.1138 | | |
| Sample 47 | 415 | 1.2371 | 9.96685797 | SCT |

Reduction in absorption

Example 6: Analysis of Blood Samples Using the Kinetics Method

This Example is a continuation of Example 5. While collecting data in Example 5, the absorbance of the samples under deoxygenated conditions was monitored across 380 nm to 600 nm for the time period shown in Table 13 below.

TABLE 13

Rate of change in absorbance

| Time in Sec | SCT | SCD | SCT RATE/MIN | SCD RATE/MIN |
|---|---|---|---|---|
| 0 | 1.01 | 0.89 | | |
| 35 | 0.98 | 0.87 | 0.040 | 0.044 |

TABLE 13-continued

Rate of change in absorbance

| Time in Sec | SCT | SCD | SCT RATE/MIN | SCD RATE/MIN |
|---|---|---|---|---|
| 70 | 0.95 | 0.83 | 0.052 | 0.067 |
| 105 | 0.92 | 0.79 | 0.052 | 0.067 |
| 140 | 0.89 | 0.75 | 0.052 | 0.067 |
| 175 | 0.86 | 0.71 | 0.052 | 0.067 |
| 210 | 0.83 | 0.67 | 0.052 | 0.067 |
| 245 | 0.80 | 0.63 | 0.052 | 0.067 |
| 280 | 0.77 | 0.59 | 0.052 | 0.067 |
| 315 | 0.74 | 0.55 | 0.052 | 0.067 |
| 350 | 0.71 | 0.51 | 0.052 | 0.067 |
| 385 | 0.68 | 0.47 | 0.052 | 0.067 |
| 420 | 0.64 | 0.42 | 0.064 | 0.091 |

It was observed that the rate of change in absorbance for the control blood sample was 0, as the absorbance did not change across the spectrum over the time period.

The rate of change in absorbance for the SCT sample was 0.052 absorbance per minute whereas the rate of change in absorbance for the SCT sample was 0.067 absorbance per minute.

Example 7: Identification of Relative Percentage of HbS in Blood Samples

This Example is a continuation of Example 5. The absorbance values under deoxygenated and oxygenated conditions measured at 425 nm ($2^{nd}$ absorbance) and 415 nm ($1^{st}$ absorbance) respectively were used to calculate the relative percentage of Hbs in the blood samples. First, a 30% of the $1^{st}$ absorbance was calculated (N). N was subtracted from the $1^{st}$ and $2^{nd}$ absorbance to obtain modified $1^{st}$ and $2^{nd}$ absorbance. To determine relative % of HbS, modified $2^{nd}$ absorbance was divided by modified first absorbance and this value was multiplied by 100. The value obtained in this was subtracted from 100 to arrive at the relative % of HbS. This is shown in Table 14 below.

TABLE 14

Calculation of relative percentage of HbS

| Sample ID | Wavelength | Absorbance | 30% of $1^{st}$ Abs (N) | Modified Absorbance | HbS Conc. Relative * | Condition |
|---|---|---|---|---|---|---|
| Control-Deoxy | 425 | 1.441 ($2^{nd}$ Abs) | | 1 ($2^{nd}$ Abs − N) | 0.0001% [100 − ((1/1.01) × 100)] | |
| Control | 415 | 1.4437 ($1^{st}$ Abs) | 0.433 | 1.01 ($1^{st}$ Abs − N) | | Normal |
| Sample-19 Deoxy | 425 | 0.6662 ($2^{nd}$ Abs) | | 0.343 ($2^{nd}$ Abs − N) | 54.02% [100 − ((0.343/0.746) × 100)] | |
| Sample-19 | 415 | 1.065 ($1^{st}$ Abs) | 0.319 | 0.746 ($1^{st}$ Abs − N) | | SCD |
| Sample-9 Deoxy | 425 | 1.0648 ($2^{nd}$ Abs) | | 0.697 ($2^{nd}$ Abs − N) | 18.39% [100 − ((0.697/0.855) × 100)] | |
| Sample-9 | 415 | 1.2211 ($1^{st}$ Abs) | 0.366 | 0.855 ($1^{st}$ Abs − N) | | SCT |
| Sample-83 Deoxy | 425 | 0.6184 ($2^{nd}$ Abs) | | 0.4 ($2^{nd}$ Abs − N) | 20.94% % [100 − ((0.4/0.506) × 100)] | |
| Sample -83 | 415 | 0.725 ($1^{st}$ Abs) | 0.217 | 0.506 ($1^{st}$ Abs − N) | | SCT |
| Sample-35 Deoxy | 425 | 1.0288 ($2^{nd}$ Abs) | | 0.598 ($2^{nd}$ Abs − N) | 40.2% % [100 − ((0.598/1.002) × 100)] | |
| Sample-35 | 415 | 1.4315 ($1^{st}$ Abs) | 0.429 | 1.002 ($1^{st}$ Abs − N) | | SCT |

TABLE 14-continued

| | | | | | | |
|---|---|---|---|---|---|---|
| | | | Calculation of relative percentage of HbS | | | |
| Sample ID | Wavelength | Absorbance | 30% of 1st Abs (N) | Modified Absorbance | HbS Conc. Relative * | Condition |
| Sample 47-Deoxy | 425 | 1.1138 (2nd Abs) | | 0.7427 (2nd Abs − N) | 14.1%% [100 − ((0.7427/0.865) × 100)] | |
| Sample 47 | 415 | 1.2371 (1st Abs) | | 0.865 (1st Abs − N) | | SCT |

Example 8: Preparation of a Kit of the Present Disclosure

A kit is prepared in accordance with the requirements of the present disclosure. The kit so prepared comprises of the following components:

a) A phosphate buffer having a concentration of 1.7-2.8M;
b) Saponin;
c) Sodium metabisulfite; and
d) an instruction manual comprising instructions to perform the method and a table providing reference threshold ratio values or reference threshold percent reduction values for the buffer included in the kit.

The kit may include blood collection tubes containing an anti-coagulant (e.g., $K_2$EDTA coated collection tubes) or lancets (if finger prick is used to collect blood) and cuvettes for measuring absorbance using a spectrophotometer.

The kit is used in the following manner to perform the Ratio Method:

a) To perform the ratio method using the kit, saponin is added to the phosphate buffer at a final concentration of 0.4% and sodium metabisulfite is added to the phosphate buffer at 2% final concentration immediately prior (e.g., about 5 minutes up to 4 hours prior) to mixing with a blood sample. The phosphate buffer comprising saponin and sodium metabisulfite is stored at 4° C. for up to 4 hours.
b) A subject's blood sample is collected in a $K_2$EDTA coated collection tube and stored at 2° C.-8° C. until the test is carried out.
c) 5 µl of subject's blood sample is mixed with 1 ml phosphate buffer comprising saponin and sodium metabisulfite. Alternatively, 5 µl of subject's blood collected by finger prick is mixed immediately with 1 ml phosphate buffer comprising saponin and sodium metabisulfite.
d) The sample-buffer mixture is incubated at room temperature for about 5 to 15 minutes.
e) After incubation, the sample-buffer mixture is loaded into a cuvette and absorbance is measured using a spectrophotometer. A first absorbance is measured at a wavelength selected from 420-440 nm and a second absorbance is measured at a wavelength selected from 545-565 nm.
f) A ratio of the second absorbance to the first absorbance or a ratio of the first absorbance to the second absorbance is calculated. The presence or absence of HbS in the blood sample and the presence or absence of SCT or SCD in the subject is determined based on the calculated ratio in view of the table provided in the instruction manual containing reference threshold ratio values.

The kit is used in the following manner to perform the Percent Reduction Method:

a) To perform the percent reduction method, two buffers are prepared using the kit. Buffer 1 is prepared by adding saponin to the phosphate buffer at 0.4% final concentration immediately prior (e.g., about 5 minutes up to 4 hours prior) to mixing with a blood sample. Buffer 2 is prepared by adding saponin (0.4%) and sodium metabisulfite (2%) to the phosphate buffer immediately prior (e.g., about 5 minutes up to 4 hours prior) to mixing with a blood sample. Both buffers are stored at 4° C. for up to 4 hours.
b) A subject's blood sample is collected in a $K_2$EDTA coated collection tube and stored at 2° C.-8° C. until the test is carried out.
c) 5 µl of subject's blood sample is mixed with 1 ml of Buffer 1 to measure a first absorbance. 5 µl of subject's blood sample is mixed with 1 ml of Buffer 2 to measure a second absorbance. Alternatively, 5 µl of subject's blood collected by finger prick is mixed immediately with 1 ml of Buffer 1 to measure a first absorbance and another 5 µl of subject's blood collected by finger prick is mixed immediately with 1 ml of Buffer 2 to measure a second absorbance.
d) The sample-buffer mixtures are incubated at room temperature for about 5 to 15 minutes.
e) After incubation, the sample-buffer mixtures are loaded into a cuvette and the absorbance is measured using a spectrophotometer. The first absorbance of the sample-Buffer 1 mixture is measured at a wavelength selected from 400-421 nm. The second absorbance of the sample-Buffer 2 mixture is measured at a wavelength selected from 422-440 nm.
f) A percent reduction in the second absorbance compared to the first absorbance is calculated. The presence or absence of HbS in the blood sample and the presence or absence of SCT or SCD in the subject is determined based on the calculated percent reduction value in view of the table provided in the instruction manual containing reference threshold percent reduction values.

The above-mentioned steps for performing each method are included in the instruction manual provided with the kit. The instruction manual also includes a reference table containing threshold ratio values or reference threshold percent reduction values for the buffer included in the kit.

We claim:

1. An in vitro method of identifying a presence or absence of sickle cell haemoglobin in a blood sample, comprising:

a. measuring a first absorbance of said blood sample under a deoxygenated condition at 420-440 nm;
b. measuring a second absorbance of said blood sample under the deoxygenated condition at 545-565 nm;
c. calculating a ratio of the second absorbance to the first absorbance or a ratio of the first absorbance to the second absorbance; and identifying the presence or absence of sickle cell haemoglobin in said blood sample based on the ratio;

wherein a difference in the ratio as compared to the same ratio measured in a blood sample containing normal haemoglobin indicates the presence of sickle cell haemoglobin in the blood sample.

2. The in vitro method of claim 1, wherein the first absorbance is measured at 420-430 nm.

3. The in vitro method of claim 1, wherein the second absorbance is measured at 550-560 nm.

4. The in vitro method of claim 1, wherein the deoxygenated condition comprises mixing said blood sample with a physiologically acceptable buffer comprising a detergent and a reducing agent.

5. The in vitro method of claim 4, wherein the physiologically acceptable buffer is selected from a phosphate buffer, a carbonate buffer, a citrate buffer, an acetate buffer, a HEPS buffer, and a MOPS buffer, the detergent is selected from saponin, sodium dodecyl sulfate (SDS), sodium lauryl sulfate (SLS), and a polysorbate; and/or the reducing agent is selected from sodium metabisulfite, sodium dithionate, disodium disulphate, sulfate tetrasodium, sodium dithionate hydrate, and sodium trithionate.

6. The in vitro method of claim 4, wherein the physiologically acceptable buffer is a phosphate buffer having a concentration of about 1.7 M - 2.8 M.

7. The in vitro method of claim 4, wherein the detergent is present at a concentration of about 0.1- 2% by weight of the physiologically acceptable buffer and/or the reducing agent is present at a concentration of about 0.5-6% by weight of the physiologically acceptable buffer.

8. The in vitro method of claim 1, wherein the ratio of the second absorbance to the first absorbance of less than 0.16 indicates the absence of sickle cell haemoglobin, or the ratio of the second absorbance to the first absorbance of 0.16 or more indicates the presence of sickle cell haemoglobin, when the deoxygenated condition comprises mixing the blood sample with 2.365M phosphate buffer comprising saponin and sodium metabisulfite to obtain a sample/buffer mixture and incubating the sample-buffer mixture for about 5-30 minutes.

9. The in vitro method of claim 1, wherein the ratio of the second absorbance to the first absorbance of less than 0.11 indicates the absence of sickle cell haemoglobin, or the ratio of the second absorbance to the first absorbance of 0.11 or more indicates the presence of sickle cell haemoglobin, when the deoxygenated condition comprises mixing the blood sample with 2.083M phosphate buffer comprising saponin and sodium metabisulfite to obtain a sample/buffer mixture and incubating the sample-buffer mixture for about 5-30 minutes.

* * * * *